US010781471B2

(12) United States Patent
Ren

(10) Patent No.: US 10,781,471 B2
(45) Date of Patent: Sep. 22, 2020

(54) NRAS RELATED CANCER THERAPY

(71) Applicants: Ruijin Hospital Affiliated to Shanghai Jiao Tong University School of Medicine, Shanghai (CN); Brandeis University, Waltham, MA (US)

(72) Inventor: Ruibao Ren, Newton, MA (US)

(73) Assignees: Ruijin Hospital Affiliated to Shanghai Jiao Tong University School of Medicine, Shanghai (CN); Brandeis University, Waltham, MA (US)

( * ) Notice: Subject to any disclaimer, the term of this patent is extended or adjusted under 35 U.S.C. 154(b) by 356 days.

(21) Appl. No.: 15/532,947

(22) PCT Filed: Dec. 4, 2015

(86) PCT No.: PCT/US2015/064048
§ 371 (c)(1),
(2) Date: Jun. 2, 2017

(87) PCT Pub. No.: WO2016/090276
PCT Pub. Date: Jun. 9, 2016

(65) Prior Publication Data
US 2017/0362633 A1 Dec. 21, 2017

Related U.S. Application Data

(60) Provisional application No. 62/239,590, filed on Oct. 9, 2015, provisional application No. 62/088,505, filed on Dec. 5, 2014.

(51) Int. Cl.
| | | |
|---|---|---|
| *C12Q 1/48* | (2006.01) | |
| *A61K 45/06* | (2006.01) | |
| *A61K 31/513* | (2006.01) | |
| *A01K 67/027* | (2006.01) | |
| *A61K 49/00* | (2006.01) | |
| *G01N 33/573* | (2006.01) | |

(52) U.S. Cl.
CPC ............ *C12Q 1/48* (2013.01); *A01K 67/0275* (2013.01); *A61K 31/513* (2013.01); *A61K 45/06* (2013.01); *A61K 49/0008* (2013.01); *C12Y 203/01* (2013.01); *C12Y 306/05002* (2013.01); *G01N 33/573* (2013.01); *A01K 2217/052* (2013.01); *A01K 2227/105* (2013.01); *A01K 2267/0331* (2013.01); *G01N 2333/914* (2013.01); *G01N 2333/91057* (2013.01); *G01N 2440/10* (2013.01); *G01N 2500/04* (2013.01); *G01N 2500/10* (2013.01); *G01N 2800/7028* (2013.01)

(58) Field of Classification Search
CPC . A61K 31/513; C12N 15/113; A01K 2207/05
See application file for complete search history.

(56) References Cited

U.S. PATENT DOCUMENTS

| | | | |
|---|---|---|---|
| 9,220,723 B2 * | 12/2015 | Ren .................... | C12N 15/1137 |
| 2005/0281785 A1 | 12/2005 | Peng et al. | |
| 2012/0258045 A1 | 10/2012 | Fitzgerald et al. | |
| 2013/0210890 A1 | 8/2013 | Ren et al. | |
| 2013/0281313 A1 * | 10/2013 | Galluzzi .............. | C12Q 1/6886 |
| | | | 506/9 |

FOREIGN PATENT DOCUMENTS

WO WO-2016/090276 A1 6/2016

OTHER PUBLICATIONS

Jennings et al. "2-Bromopalmitate and 2-(2-hydroxy-5-nitro-benzylidene)-benzo[b]thiophen-3-one inhibit DHHC-mediated palmitoylation in vitro." J Lipid Res. Feb. 2009;50(2):233-42. (Year: 2009).*
Mansilla et al. "Differential expression of DHHC9 in microsatellite stable and instable human colorectal cancer subgroups." Br J Cancer. Jun. 18, 2007;96(12):1896-903. (Year: 2007).*
Cuiffo et al., Palmitoylation of oncogenic NRAS is essential for leukemogenesis, Blood, 115: 3598-3605 (2010).
International Search Report for PCT/US2015/064048, 3 pages (dated Apr. 21, 2016).
Jennings et al., 2-Bromopalmitate and 2-(2-hydroxy-5-nitro-benzylidene)-benzo[b] thiophen-3-one inhibit DHHC-mediated palmitoylation in vitro, J. Lipid Res., 50: 233-42 (2008).
Liu et al., Role of RAS palmitoyl'acyltransferase DHHCg in hematopoiesis and NRAS leukemogenesis, Mol Cancer Res, 12: 1 (2014).
Written Opinion for PCT/US2015/064048, 9 pages (dated Apr. 21, 2016).

* cited by examiner

*Primary Examiner* — Brian Whiteman
(74) *Attorney, Agent, or Firm* — Choate, Hall & Stewart LLP; Brenda Herschbach Jarrell; Michael L. Vetter

(57) ABSTRACT

The present invention encompasses the recognition that identification of alternative means to block RAS oncogenic signaling may be required for developing novel cancer therapies. Among other things, the present invention encompasses the recognition that targeting RAS palmitoylation can achieve effective therapy for RAS-related cancers. Furthermore, the present invention encompasses the recognition that reduction of ZDHHC9 level and/or activity can significantly reduce palmitoylation level of Ras protein. Among other things, the present invention encompasses the recognition that identification of agents that modulate expression and/or activity of ZDHHC9 can reduce palmitoylation level of Ras protein. In some embodiments, the present invention provides methods of treating a subject suffering from cancer by administering ZDHHC9 inhibition therapy.

9 Claims, 7 Drawing Sheets

FIG. 2A
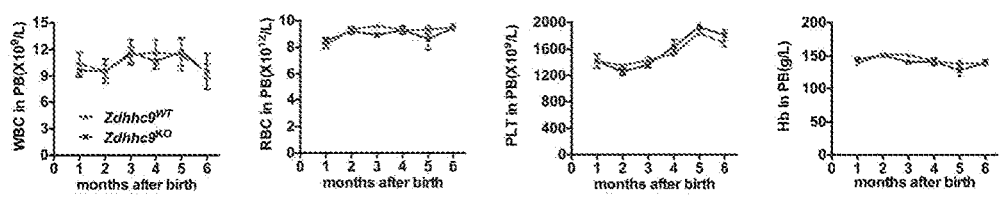
FIG. 2B
FIG. 2C
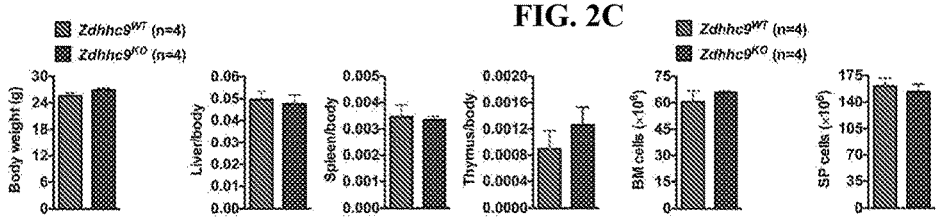
FIG. 2D
FIG. 2E
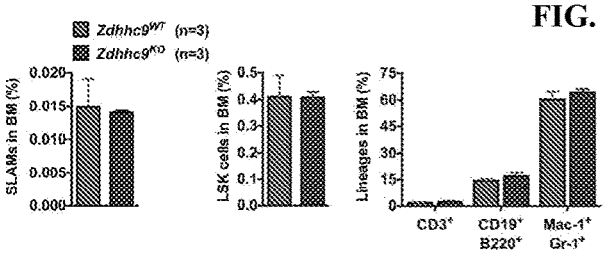
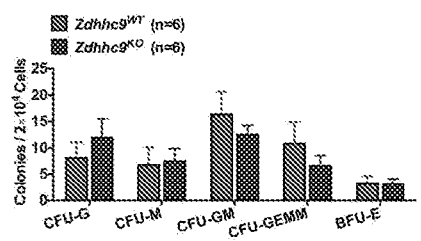

NRAS RELATED CANCER THERAPY

CROSS REFERENCE TO RELATED APPLICATIONS

The present application claims priority to U.S. provisional application Ser. No. 62/088,505, filed Dec. 5, 2014 and U.S. provisional application Ser. No. 62/239,590, filed Oct. 9, 2015, each of which is hereby incorporated by reference in its entirety.

BACKGROUND

The American Cancer Society estimates that more than 1.6 million new cases of cancer will be diagnosed in 2015. A powerful need exists for new therapies and novel approaches to their identification and development.

SUMMARY

The present invention encompasses the recognition that hyperactivation of RAS family members is common in many human cancers. Furthermore, the present invention encompasses the recognition that palmitoylation of RAS proteins, e.g. NRAS, often contributes to, and may be required for, leukemogenesis. As RAS proteins are difficult to target, the present invention encompasses the recognition that identification of alternative means to block RAS oncogenic signaling may be required for developing novel cancer therapies. Among other things, the present invention encompasses the recognition that targeting RAS palmitoylation can achieve effective therapy for RAS-related cancers. Furthermore, the present invention encompasses the recognition that reduction of ZDHHC9 level and/or activity can significantly reduce palmitoylation level of Ras protein. Among other things, the present invention encompasses the recognition that identification of agents that modulate expression and/or activity of ZDHHC9 can reduce palmitoylation level of Ras protein. In some embodiments, the present invention provides methods of treating a subject suffering from cancer by administering ZDHHC9 inhibition therapy.

In some embodiments the present invention provides methods of identifying one or more ZDHHC9 inhibitors. In some embodiments one or more inhibitors are identified by contacting a model system in which ZDHHC9 activity, or a proxy thereof, is detectable with a plurality of test agents; detecting ZDHHC9 activity, or the proxy thereof, in the model system when each test agent is present; comparing detected ZDHHC9 activity, or the proxy thereof, to an appropriate reference ZDHHC9 activity or proxy thereof; identifying a test agent as a ZDHHC9 inhibitor when the detected activity or proxy thereof is reduced relative to the reference activity or proxy thereof.

In some embodiments the present invention provides methods of reducing incidence and severity of negative chemotherapy side effects. In some embodiments incidence and severity of negative chemotherapy side effects are reduced by administering to a subject suffering from or susceptible to one or more negative chemotherapy side effects an amount of ZDHHC9 inhibition therapy sufficient to delay onset of or reduce one or more of incidence and severity of the negative chemotherapy side effects.

BRIEF DESCRIPTION OF THE DRAWING

FIG. 1A presents a schematic diagram of gene knockout strategy of the X-linked Zdhhc9 gene (NM_172465). Wild type (WT), targeting vector (pKOS-90), as well as mutant (MT) alleles shown before and after homologous recombination. The red box depicts a LacZ/Neo selective cassette inserted into the exon 2, which replaces a 206-bp genomic DNA fragment that harbors the start codon of the gene. The "ATG" codon is marked by a pentagram symbol. Primers (P1, 2, 5, 6 and Neo) are used to distinguish WT and MT genomic loci and mRNA transcripts of the Zdhhc9 gene.

FIG. 1B demonstrates genotyping of genomic DNA isolated from tails of $Zdhhc9^{WT}$ and $Zdhhc9^{KO}$ mice. The combination of P5, P6 and Neo primers is used for the genotypic analysis. The WT-specific product amplified by P5 and P6 primers is 225 bp in length, while MT-specific one amplified by Neo and P6 primers is 203 bp in length.

FIG. 1C depicts RT-PCR analysis of Zdhhc9 transcripts in BM and spleen from both $Zdhhc9^{WT}$ and $Zdhhc9^{KO}$ mice. The pair of primers P1 and P2 that spans the Exon 2 and 3 is used for distinguishing the WT and MT transcripts, using Gapdh gene expression as the internal control.

FIG. 1D shows Western blot analysis of Zdhhc9 protein expression in BM and spleen cells from $Zdhhc9^{WT}$ and $Zdhhc9^{KO}$ mice. The asterisk (*) denotes the non-specific bands in the blots using a Zdhhc9 antibody. β-Actin was used as a loading control.

FIG. 1E shows Ras palmitoylation levels in BM cells of $Zdhhc9^{WT}$ and $Zdhhc9^{KO}$ mice. The ABE assay was used to detect Ras palmitoylation levels. Palmitoylated proteins extracted from BM cells of $Zdhhc9^{WT}$ and $Zdhhc9^{KO}$ mice were biotinylated and precipitated by streptavidin-coated agarose beads, followed by western blot analysis using the RAS10 antibody. The intensity of each Ras specific band was analyzed by NIH ImageJ software. The relative Ras palmitoylation levels were evaluated by dividing the Ras protein level in precipitates by the total Ras protein level before precipitation. The ratios of each sample were normalized by the value of Ras palmitoylation in wild-type BM. Samples without hydroxylamine treatment were used as negative controls for non-specific streptavidin binding. +HA or −HA: with or without hydroxylamine treatment.

FIGS. 2A-2E demonstrate that Zdhhc9 inactivation does not affect normal hematopoiesis under homeostatic conditions. Data are representative of 3 independent experiments.

FIG. 2A shows results of blood tests that were conducted monthly in 6-month period. WBC, white blood cell; RBC, red blood cell; PLT, platelet; Hb, hemoglobin. Mean±SEM; $Zdhhc9^{WT}$ n=3-8; $Zdhhc9^{KO}$, n=4-10.

FIG. 2B shows comparison of body weight and organ size of hematological tissues between $Zdhhc9^{WT}$ and $Zdhhc9^{KO}$ mice. 16-week-old male $Zdhhc9^{WT}$ and $Zdhhc9^{KO}$ littermates were scarified for the analysis. The vertical axis shows the ratio of organ weight to body weight. Mean±SEM; n=4 in each group.

FIG. 2C shows comparison of cellularity of BM and spleen between $Zdhhc9^{WT}$ and $Zdhhc9^{KO}$ mice as (b). BM, bone marrow; SP, spleen. Mean±SEM; n=4 in each group.

FIG. 2D shows immunophenotyping of hematopoietic stem cells (HSCs) and lineage specific cells in BM from $Zdhhc9^{WT}$ and $Zdhhc9^{KO}$ mice. LSKs, HSCs defined as Lineage$^-$/Sca1$^+$/c-Kit$^+$; SLAMs, Long-term HSCs defined as CD150$^+$/CD48$^-$/Lineage$^-$/Sca1$^+$/c-Kit$^+$. Lineage-mixed markers include Mac-1, Gr-1, B220, CD3 and Ter119. Mean±SEM; n=3 in each group.

FIG. 2E shows quantification of colonies formed by BM cells from between $Zdhhc9^{WT}$ and $Zdhhc9^{KO}$ mice in M3434 medium at Day 12. Mean±SEM; n=6 in each group.

FIG. 3A shows blood counts monitored every 3 days after single dose of 5-FU (150 mg/kg) treatment in Zdhhc9$^{WT}$ and Zdhhc9$^{KO}$ mice. Mean±SEM; n=3 in each group.

FIG. 3B shows blood counts monitored every 3 days after two doses of 5-FU (150 mg/kg each) treatment in Zdhhc9$^{WT}$ and Zdhhc9$^{KO}$ mice. Mean±SEM; n=5 in each group.

FIG. 3C shows the survival curve of Zdhhc9$^{WT}$ and Zdhhc9$^{KO}$ mice receiving serial 5-FU treatment. Mean±SEM; n=5 in each group.

FIG. 4A shows quantitative analysis of colonies formed by GFP-NRAS$^{G12D}$-transduced Zdhhc9$^{WT}$ and Zdhhc9$^{KO}$ BM cells in M3434 medium on Day 7. Mean±SEM; n=3 in each group; P=0.0167 for CFU-GM and P=0.0222 for all CFUs counts, respectively.

FIG. 4B shows Representative images of colonies formed by GFP-NRAS$^{G12D}$-transduced Zdhhc9$^{WT}$ and Zdhhc9$^{KO}$ BM cells. Left panel: bright-filed view; right panel, GFP signals. Scale bar, 100 μm; the original magnification was ×200.

FIG. 4C shows Live imaging of GFP-NRAS$^{G12D}$- or GFP-NRAS$^{G12D/C181S}$-transduced BM cells by confocal microscopy. Representative data are shown. Scale bar, 20 μm; the original magnification was ×630.

FIG. 4D shows Palmitoylation of GFP-NRAS$^{G12D}$ in GFP-NRAS$^{G12D}$-transduced Zdhhc9$^{WT}$ and Zdhhc9$^{KO}$ BM cells detected by the ABE method.

FIG. 5A shows an Experimental scheme for the induction of T-ALL by oncogenic Nras in Zdhhc9$^{WT}$ and Zdhhc9$^{KO}$ mice. A week after the 2 doses pIpC treatment, 2×10$^5$ BM cells from the Mx1-Cre;Nras$^{LSL-G12D/LSL-G12D}$;Zdhhc9$^{KO}$ or Mx1-Cre;Nras$^{LSL-G12D/LSL-G12D}$;Zdhhc9$^{WT}$ mice (CD45.2) were combined with the equal amount of competitor BM cells (CD45.1) and injected into lethally irradiated wild-type recipients (CD45.1).

FIG. 5B shows Kaplan-Meier survival curves of recipient mice of Nras$^{G12D/G12D}$;Zdhhc9$^{KO}$ and Nras$^{G12D/G12D}$;Zdhhc9$^{WT}$ donor BM cells. The median survival is 202 and 390 days for Zdhhc9$^{WT}$ and Zdhhc9$^{KO}$ recipients, respectively. P=0.0013; n=19 in each group.

FIG. 5C shows representative FACS plots of thymic leukemia cells isolated from moribund Nras$^{G12D/G12D}$;Zdhhc9$^{KO}$ and Nras$^{G12D/G12D}$;Zdhhc9$^{WT}$ recipient mice by flow cytometry. Nras$^{+/+}$;Zdhhc9$^{WT}$ mice were used as a control.

FIG. 5D shows an experimental scheme for the induction of MPN by oncogenic Nras in Zdhhc9$^{WT}$ and Zdhhc9$^{KO}$ mice.

FIG. 5E shows Kaplan-Meier survival curves of Nras$^{G12D/G12D}$;Zdhhc9$^{KO}$ and Nras$^{G12D/G12D}$;Zdhhc9$^{WT}$ mice after s administration. The median survivals were 152 vs. 173 days for Nras$^{G12D/G12D}$;Zdhhc9$^{WT}$ (n=12) and Nras$^{G12D/G12D}$;Zdhhc9$^{KO}$ (n=10) mice, respectively. P=0.0478.

FIG. 5F shows representative FASC plots of BM and spleen cells from diseased Nras$^{G12D/G12D}$;Zdhhc9$^{WT}$ and Nras$^{G12D/G12D}$;Zdhhc9$^{KO}$ mice.

FIG. 6A shows RT-qPCR analysis of mRNA expression levels of Zdhhc family genes in different hematopoietic cell lineages from BM of wild-type C57BL/6 mice. The y axis indicates gene expression data expressed as $2^{-\Delta CT = CT(Zdhhc\ gene) - CT(Gapdh)}$. Mean±SEM; n=4 in each group.

FIG. 6B shows RT-qPCR analysis of mRNA expression of Zdhhc family genes in BM cells from Zdhhc9$^{WT}$ and Zdhhc9$^{KO}$ mice. Mean±SEM; n=4 in each group.

FIG. 6C shows RT-qPCR analysis of mRNA expression of Zdhhc family genes in BM cells from Zdhhc9$^{WT}$ and Zdhhc9$^{KO}$ mice in the Nras$^{G12D/G12D}$ background. Mean±SEM; n=3 in each group.

DEFINITIONS

Figure 1A:
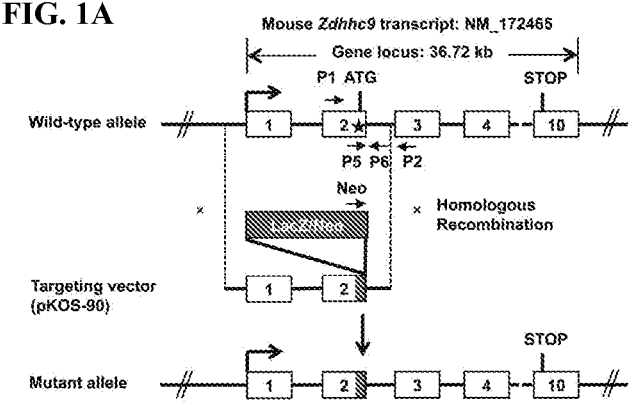
FIGS. 1A-1E depict characterization of Zdhhc9 knockout mice. Data are representative of 3 independent experiments.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form.

In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Animal: as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises an antibody-drug conjugate.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Cancer: The terms "cancer", "malignancy", "neoplasm", "tumor", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastrointestinal cancers and nervous system cancers, benign lesions such as papillomas, and the like.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhihitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG -7598, RG-7599, RG-7600, RG-7636, ABT-414, IMGN-853, IMGN-529, vorsetuzumab mafodotin, and lorvotuzumab mertansine. In some embodiments, a chemotherapeutic agent may be one described as utilized in an antibody-drug conjugate as described or discussed in one or more of Govindan et al, The Scientific World Journal 10:2070, 2010,-2089.

In some embodiments, a chemotherapeutic agent may be or comprise one or more of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Determine: Some methodologies described herein include a step of "determining" Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Ex Vivo: As used herein refers to events that occur in or on tissue from a multi-cellular organism, such as a human and a non-human animal, in an external environment which resembles the natural conditions of the tissue with a minimum of alterations to the tissue itself Human: In some embodiments, a human is an embryo, a fetus, an infant, a child, a teenager, an adult, or a senior citizen.

Improve," "increase" or "reduce: as used herein or grammatical equivalents thereof, indicate values that are relative to a baseline measurement, such as a measurement in the same individual or model system prior to initiation of a treatment or introduction of a test agent described herein, or a measurement in a control individual (or multiple control individuals) in the absence of the treatment described herein. In some embodiments, a "control individual" is an individual afflicted with the same form of disease or injury as an individual being treated.

Inhibitor: As used herein, the term "inhibitor" refers to an agent, condition, or event whose presence, level, degree, type, or form correlates with decreased level or activity of another agent (i.e., the inhibited agent, or target). In general, an inhibitor may be or include an agent of any chemical class including, for example, small molecules, polypeptides, nucleic acids, carbohydrates, lipids, metals, and/or any other entity, condition or event that shows the relevant inhibitory activity. In some embodiments, an inhibitor may be direct (in which case it exerts its influence directly upon its target, for example by binding to the target); in some embodiments, an inhibitor may be indirect (in which case it exerts its influence by interacting with and/or otherwise altering a regulator of the target, so that level and/or activity of the target is reduced).

In vitro: as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Nucleic acid: as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Polypeptide: as used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Protein: As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In some embodiments "protein" can be a complete polypeptide as produced by and/or active in a cell (with or without a signal sequence); in some embodiments, a "protein" is or comprises a characteristic portion such as a polypeptide as produced by and/or active in a cell. In some embodiments, a protein includes more than one polypeptide chain. For example, polypeptide chains may be linked by one or more disulfide bonds or associated by other means. In some embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In some embodiments, proteins or polypeptides may comprise natural amino acids, non-natural amino acids, synthetic amino acids, and/or combinations thereof. In some embodiments, proteins are or comprise antibodies, antibody polypeptides, antibody fragments, biologically active portions thereof, and/or characteristic portions thereof.

Reference: as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Those of ordinary skill in the art, reading the present disclosure, will appreciate that certain small molecule compounds described herein may be provided and/or utilized in any of a variety of forms such as, for example, salt forms, protected forms, pro-drug forms, ester forms, isomeric forms (e.g., optical and/or structural isomers), isotopic forms, etc. In some embodiments, reference to a particular compound may relate to a specific form of that compound. In some embodiments, reference to a particular compound may relate to that compound in any form. In some embodiments, where a compound is one that exists or is found in nature, that compound may be provided and/or utilized in accordance in the present invention in a form different from that in which it exists or is found in nature. Those of ordinary skill in the art will appreciate that a compound preparation including a different level, amount, or ratio of one or more individual forms than a reference preparation or source (e.g., a natural source) of the compound may be considered to be a different form of the compound as described herein. Thus, in some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form; etc.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen", as that term is used herein, refers to a dosing regimen whose administration across a relevant population may be correlated with a desired or beneficial therapeutic outcome.

Treatment: As used herein, the term "treatment" (also "treat" or "treating") refers to any administration of a substance (e.g., chemotherapeutic, ZDHHC9 inhibitor) that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Palmitoylation

In some embodiments, methods of the present invention relate to palmitoylation. Palmitoylation is the covalent attachment of fatty acids, such as palmitic acid, to cysteine, serine, and threonine residues of proteins. Palmitoylation enhances the hydrophobicity of proteins and contributes to their membrane association. Palmitoylation also appears to play a role in subcellular trafficking of proteins between membrane compartments, as well as in modulating protein-protein interactions. S-palmitoylation, which is the covalent lipid modification of the side chain of cysteine residues with the 16-carbon fatty acid palmitate, is catalyzed by palmitoylacyltransferases (PATs).

ZDHHC9

Transferase is the general name for the class of enzymes that enact the transfer of specific functional groups (e.g. methyl, glycosyl, palmityl, etc.) from one molecule to another. In some embodiments, the present invention relates to palmitoylacyltransferases (PATs). To date, at least 23 mammalian PATs have been identified.[12-14] RAS PAT was first discovered by genetic studies in yeast. An Erf2-Erf4 PAT complex was identified in a yeast genetic screen based on the loss of function of a palmitoylation-dependent Ras2 allele.[15,6] Erf2 is a transmembrane protein containing an aspartate-istidine-histidine-cysteine (DHHC) conserved motif embedded in a cysteine-rich domain, which participates in enzymatic activity.[17]

In some embodiments, the present invention relates to mammalian orthologs of Erf2 and/or Erf4. In mammals, Zinc finger DHHC-type containing 9 (ZDHHC9, a transmembrane protein) and Golgi-complex associated protein of 16 kDa (GCP16) are functional orthologs of Erf2 and Erf4 respectively, and constitute a PAT complex with specificity for both NRAS and HRAS in vitro.[18,19] ZDHHC9 has been shown to be upregulated in many human cancers.[1,16, 20] Yet, prior to the present disclosure, the physiological and pathological role(s) of ZDHHC9 in vivo were not known.

RAS Family

In some embodiments, methods of the present invention relate to RAS protein family members. The Ras superfamily can include but is not limited to RAS, Rho, Ran, Rab and Arf.

The RAS family proteins, including NRAS, HRAS, KRAS4A and KRAS4B, are small GTPases that act as molecular switches, transducing signals from many activated receptors that regulate cell proliferation, survival, and differentiation[1,2] RAS mutations are most frequent among proto-oncogenes in human cancer, including hematological malignances.[2] However, owning to extremely high affinity to GTP and relatively smooth structural surface of RAS oncoproteins, RAS is hard to target.[3-5]

RAS proteins undergo several post-translation modifications (PTMs) to mature into fully functional molecules on the inner leaflet of plasma membrane (PM).[6,7] One potential approach to block the RAS oncogenic signaling is, therefore, to inhibit RAS translocation to the plasma membrane.[6-9] Much emphasis had been placed on developing therapies targeting RAS prenylation, but successes are modest to date due to a redundancy of the two RAS prenylation enzymes, i.e. farnesferase (FTase) and geranylgeranyltransferase (GG-Tase).[10,11]

As is known in the art, members of the RAS subfamily plays a role in regulation of cell proliferation. As is also known, certain mutations in RAS subfamily proteins can lead to constitutively active proteins. In some cases, constitutive RAS activity can lead to cancer. RAS oncogenic mutations, mostly KRAS and NRAS, are common in human cancers. Since the enzymatic activity of RAS is used to turn itself off and its GTP binding affinity is very high, RAS proteins have been difficult to target. Identification of alternative means to block the RAS oncogenic signaling is useful for developing therapies against RAS-driven cancer.

NRAS

In some embodiments, the present invention relates to palmitoylation of NRAS. In some embodiments, the present invention relates to identifying inhibitors of NRAS palmitoylation. In some embodiments, the present invention relates to treatment of cancer by administering to a patient in need thereof an agent that inhibits palmitoylation of NRAS.

NRAS is involved in cell division. NRAS which has intrinsic GTPase activity, is activated by a guanine nucleotide-exchange factor and inactivated by a GTPase activating protein. NRAS shuttles between the Golgi apparatus and the plasma membrane. This shuttling is regulated through palmitoylation and depalmitoylation by ZDHHC9. Mutations in this gene have been associated with numerous cancers.

Cancers

The present disclosure relates particularly to cancers characterized by one or more alterations in RAS level and/or activity. In some embodiments, the present disclosure relates particularly to cancers characterized by one or more RAS mutations. In some embodiments, the present disclosure relates particularly to cancers characterized by one or more alterations in NRAS level and/or activity. In some embodiments, the present disclosure relates particularly to cancers characterized by one or more NRAS mutations.

In some embodiments, the present disclosure relates to cancers of the blood or lymph. In some embodiments, the present disclosure relates to cancers of solid organs. In some embodiments, the present disclosure relates to one or more of liver cancer, lung cancer, colorectal cancer, multiple myeloma, melanoma, lymphoma and leukemia. The present disclosure relates particularly to Chronic Myelomonocytic Leukemia (CMML), B and T-cell Acute Lymphoblastic Leukemia (B-ALL and T-ALL), Acute Myeloid Leukemia (AML), Juvenile Myelomonocytic Leukemia (JMML), and Acute B Lymphoblastic Leukemia (B-ALL).

Liver Cancer

In some embodiments, the present invention relates to treatment of liver cancer. Liver cancer, also known as hepatic cancer, is a cancer that originates in the liver. Liver tumors are discovered on medical imaging equipment or present themselves symptomatically as an abdominal mass, abdominal pain, yellow skin, nausea or liver dysfunction.

The most frequent liver cancer, accounting for approximately 75% of all primary liver cancers, is hepatocellular carcinoma (HCC) (also named hepatoma, which is a misnomer because adenomas are usually benign). HCC is a cancer formed by liver cells, known as hepatocytes, that become malignant. Another type of cancer formed by liver cells is hepatoblastoma, which is specifically formed by immature liver cells. It is a rare malignant tumor that primarily develops in children, and accounts for approximately 1% of all cancers in children and 79% of all primary liver cancers under the age of 15. Most hepatoblastomas form in the right lobe.

Liver cancer can also form from other structures within the liver such as the bile duct, blood vessels and immune cells. Cancer of the bile duct (cholangiocarcinoma and cholangiocellular cystadenocarcinoma) account for approximately 6% of primary liver cancers. There is also a variant type of HCC that consists of both HCC and cholangiocarcinoma. Tumors of the blood vessels (angiosarcoma and hemangioendothelioma, embryonal sarcoma and fibrosarcoma) are produced from a type of connective tissue known as mesenchyme. Cancers produced from muscle in the liver are leiomyosarcoma and rhabdomyosarcoma. Other less common liver cancers include carcinosarcomas, teratomas, yolk sac tumors, carcinoid tumors and lymphomas. Lymphomas usually have diffuse infiltration to liver, but may also form a liver mass in rare occasions.

Lung Cancer

In some embodiments, the present invention relates to treatment of lung cancer. Lung cancer, also known as carcinoma of the lung or pulmonary carcinoma, is a malignant lung tumor characterized by uncontrolled cell growth in tissues of the lung. If left untreated, this growth can spread beyond the lung by process of metastasis into nearby tissue or other parts of the body. Most cancers that start in the lung, known as primary lung cancers, are carcinomas that derive from epithelial cells. Similar to many other cancers, lung cancer is initiated by activation of oncogenes or inactivation of tumor suppressor genes. In some cases, carcinogens may cause mutations in such genes, resulting in development of cancer.

The main primary types are small-cell lung carcinoma (SCLC) and non-small-cell lung carcinoma (NSCLC). Non-small cell lung cancer accounts for about 85 percent of lung cancers. Among them are these types of tumors:

Adenocarcinoma is the most common form of lung cancer in the United States among both men and women.

Squamous cell carcinoma (which is also called epidermoid carcinoma) forms in the lining of the bronchial tubes.

Large cell carcinomas refer to non-small cell lung cancers that are neither adenocarcinomas nor epidermoid cancers.

Small cell lung cancer accounts for the remaining 15 percent of lung cancers in the United States. Small cell lung cancer results from smoking even more so than non-small cell lung cancer, and grows more rapidly and spreads to other parts of the body earlier than non-small cell lung cancer. It is also more responsive to chemotherapy.

Colorectal Cancer

In some embodiments, the present invention relates to treatment of lung cancer. Colorectal cancer (also known as colon cancer, rectal cancer, or bowel cancer) is the development of cancer in the colon or rectum (parts of the large intestine). Colorectal cancer arises due to abnormal growth of cells that have the ability to invade or spread to other parts of the body. Signs and symptoms may include blood in the stool, a change in bowel movements, weight loss, and feeling tired all the time.

Risk factors for colorectal cancer include lifestyle, older age, and inherited genetic disorders. Other risk factors include diet, smoking, alcohol, lack of physical activity, family history of colon cancer and colon polyps, presence of colon polyps, race, exposure to radiation, and even other diseases such as diabetes and obesity. Genetic disorders only occur in a small fraction of the population. A diet high in red, processed meat, while low in fiber increases the risk of colorectal cancer. Other diseases such as inflammatory bowel disease, which includes Crohn's disease and ulcerative colitis, can increase the risk of colorectal cancer. Some inherited genetic disorders that can cause colorectal cancer include familial adenomatous polyposis and hereditary non-polyposis colon cancer; however, these represent less than 5% of cases. It typically starts as a benign tumor, often in the form of a polyp, which over time becomes cancerous.

Multiple Myeloma

In some embodiments, the present invention relates to treatment of multiple myeloma. Multiple myeloma, also known as plasma cell myeloma, myelomatosis, or Kahler's disease, is a cancer of plasma cells, a type of white blood cell normally responsible for producing antibodies. In multiple myeloma, collections of abnormal plasma cells accumulate in the bone marrow, where they interfere with the production of normal blood cells. Most cases of multiple myeloma also feature the production of a paraprotein—an abnormal antibody which can cause kidney problems. Bone lesions and hypercalcemia (high blood calcium levels) are also often encountered.

Melanoma

In some embodiments, the present invention relates to treatment of melanoma. Melanoma, (e.g. malignant melanoma), is a type of cancer that develops from the pigment-containing cells known as melanocytes. Melanomas typically occur in the skin but may rarely occur in the mouth, intestines, or eye. In women they most commonly occur on the legs, while in men they are most common on the back. Sometimes they develop from a mole with concerning changes including an increase in size, irregular edges, change in color, itchiness, or skin breakdown.

The primary typical cause of melanoma is ultraviolet light (UV) exposure in those with low levels of skin pigment. The UV light may be from either the sun or from tanning devices. About 25% develop from moles. Those with many moles, a history of affected family members, and who have poor immune function are at greater risk. A number of rare genetic defects such as xeroderma pigmentosum also increase risk. Diagnosis is by biopsy of any concerning skin lesion.

Chronic Myelomonocytic Leukemia (CMML)

In some embodiments, methods of the present invention relate to the treatment of chronic myelomonocytic leukemia (CMML). CMML is a type of leukemia. In CMML, there are increased numbers of monocytes and immature blood cells (blasts) in the peripheral blood and bone marrow, as well as abnormal looking cells (dysplasia) in at least one type of blood cell. CMML shows characteristics of a myelodysplastic syndrome (MDS); a disorder that produces abnormal looking blood cells, and a myeloproliferative disorder (MPD); a disorder characterized by the overproduction of blood cells. KRAS and NRAS are mutated in 25-40% of the cases of CMML.

Acute Lymphoblastic Leukemia (T-ALL and B-ALL)

In some embodiments, methods of the present invention relate to the treatment of acute lymphoblastic leukemia relating to T- cells (T-ALL) and/ or B-cells (B-ALL). T-ALL is a form of lymphoid leukemia and lymphoma in which too many T-cell lymphoblasts (immature white blood cells) are found in the blood, bone marrow, and tissues, particularly mediastinal lymph nodes. B-ALL is a clonal malignant disease originated in a single cell and characterized by the accumulation of blast cells that are phenotypically reminiscent of normal stages of B-cell differentiation. Among acute leukemia, T-ALL accounts for about 15% of pediatric cases and 20% of adults cases. As detected by conventional cytogenetic methods, patients with T-ALL have a smaller percentage of abnormal clones (60%-70%) than do patients with B- ALL (80%-90%). Tetraploidy is observed in about 3% of patients with T-ALL, but it has no known prognostic significance. Cytogenetic abnormalities that are common in B- ALL (e.g., high-hyperdiploidy) are uncommon in T-cell ALL. Many of the translocations seen in T-ALL are recurrent but with a low frequency. Mutations in NRAS and KRAS are highly prevalent in acute lymphoblastic leukemias.

Acute Myeloid Leukemia (AML)

In some embodiments, methods of the present invention relate to the treatment of acute myeloid leukemia (AML) AML is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for roughly 1.2% of cancer deaths in the United States, its incidence is expected to increase as the population ages.

Juvenile Myelomonocytic Leukemia (JMML)

In some embodiments, methods of the present invention relate to the treatment juvenile yyelomonocytic leukemia (JMML). JMML is a serious chronic leukemia (cancer of the blood) that affects children mostly aged 4 and under. The average age of patients at diagnosis is 2 years old. The World Health Organization has categorized JMML as a mixed myelodysplastic and myeloproliferative disorder. The name JMML encompasses all diagnoses formerly referred to as Juvenile Chronic Myeloid Leukemia (JCML), Chronic Myelomonocytic Leukemia of Infancy, and Infantile Monosomy 7 Syndrome.

JMML accounts for 1-2% of childhood leukemias each year; in the United States, there are an estimated 1-2 cases per million children. There is no known environmental cause for JMML. Since about 10% of patients are diagnosed before 3 months of age, it is thought that JMML is a congenital condition in these infants.

Approximately 90% of JMML patients have some sort of genetic abnormality in their leukemia cells that can be identified with laboratory testing. This includes:

10% of patients with inborn mutations in the CBL gene

15% of patients with neurofibromatosis 1 (NF1)

25% of patients with mutations in one of the RAS family of oncogenes (only in their leukemia cells)

Another 35% of patients with a mutation in a gene called PTPN11 (again, only in their leukemia cells)

Chemotherapy Regimens

In some embodiments, the present invention relates to subjects who are or have received a chemotherapeutic regimen. Those of ordinary skill in the art are familiar with a variety of chemotherapeutic agents for which approved or recommended treatment protocols are established. In some embodiments, a particular agent may be administered in accordance with such an approved or recommended treatment protocol (which may be referred to herein as a "reference" protocol for the particular agent); in some embodiments, however, teachings of the present disclosure permit development and/or use of alternative regimens, including for example combination therapy regimens in which one or more individual doses, dosing intervals, number and/or frequency of courses, etc may be modified (e.g., may be reduced), for example in accordance with some embodiments of a combination therapy regimen as described herein. Below are summaries of certain reference protocols for particular exemplary agents:

Fluoracil

Fluoracil injection should be administered intravenously. Twelve mg/kg of fluoracil are given intravenously once daily for four successive days. The daily dose should not exceed 800 mg. If no toxicity is observed, 6 mg/kg are given on the 6th, 8th, 10th and 12th days unless toxicity occurs. No therapy is given on the 5th, 7th, 9th or 11th days. Therapy is to be discontinued at the end of the 12th day, even if no toxicity has become apparent.

Vincristine

Vincristine is administered intravenously at weekly intervals. The recommended dose is 1.4 to 1.5 mg/m$^2$ up to a maximum weekly dose of 2 mg. The dosage must always be adjusted individually because of the narrow range between therapeutic and toxic levels, and individual variations in response.

Doxorubicin

The recommended dosage schedule for doxorubicin is 60-75 mg/m2 as a single intravenous injection administered at 21 day intervals. The lower dose should be given to patients with inadequate marrow reserves due to old age, or prior therapy, or neoplastic marrow infiltration. An alternative dose schedule is 30 mg/m2 on each of three successive days repeated every 4 weeks. The adult dosage regimens may be suitable for pediatric cases. The recommended lifetime cumulative dose limit is 550 mg doxorubicin /m$^2$ body surface area. Doxorubicin has been administered as an intra-arterial infusion for 1-3 days at doses of 45-100 mg/m$^2$. It is recommended that the total cumulative dose of doxorubicin for adults aged 70 or older be restricted to 450 mg/m2 body surface area.

Cyclophosphamide

An initial intravenous course of cyclophosphamide for patients with no hematologic deficiency comprises 40 mg per kg to 50 mg per kg in divided doses over 2 to 5 days. Other regimens include 10 mg per kg to 15 mg per kg given every 7 to 10 days or 3 mg per kg to 5 mg per kg twice weekly.

Oral dosing of cyclophosphamide usually comprises 1 mg per kg per day to 5 mg per kg per day for both initial and maintenance dosing.

L-Asparaginase

As a component of selected multiple agent induction regimens, L-asparaginase may be administered by either the intravenous or the intramuscular route. When administered intravenously this enzyme should be given over a period of not less than thirty minutes through the side arm of an already running infusion of Sodium Chloride Injection or Dextrose Injection 5% (DsW). When administering L-asparaginase intramuscularly, the volume at a single injection site should be limited to 2 mL. If a volume greater than 2 mL is to be administered, two injection sites should be used.

Recommended Induction Regimens for L-asparaginase:

When using chemotherapeutic agents in combination for the induction of remissions in patients with acute lymphocytic leukemia, regimens are sought which provide maximum chance of success while avoiding excessive cumulative toxicity or negative drug interactions.

One of the following combination regimens incorporating L-asparaginase is recommended for acute lymphocytic leukemia in pediatric patients:

In the regimens below, Day 1 is considered to be the first day of therapy.

Regimen 1:

Prednisone 40 mg/square meter of body surface area per day orally in three divided doses for 15 days, followed by tapering of the dosage as follows:

20 mg/square meter for 2 days, 10 mg/square meter for 2 days, 5 mg/square meter for 2 days, 2.5 mg/square meter for 2 days and then discontinue. Vincristine sulfate 2 mg/square meter of body surface area intravenously once weekly on Days 1, 8, and 15 of the treatment period. The maximum single dose should not exceed 2.0 mg. Asparaginase 1,000 I.U./kg/day intravenously for ten successive days beginning on Day 22 of the treatment period.

Regimen II

Prednisone 40 mg/square meter of body surface area per day orally in three divided doses for 28 days (the total daily dose should be to the nearest 2.5 mg), following which the dosage of prednisone should be discontinued gradually over a 14 day period.

Vincristine sulfate 1.5 mg/square meter of body surface area intravenously weekly for four doses, on Days 1, 8, 15, and 22 of the treatment period. The maximum single dose should not exceed 2.0 mg. Asparaginase 6,000 I.U./square meter of body surface area intramuscularly on Days 4, 7, 10, 13, 16, 19, 22, 25, and 28 of the treatment period. When a remission is obtained with either of the above regimens, appropriate maintenance therapy must be instituted. L-asparaginase should not be used as part of a maintenance regimen. The above regimens do not preclude a need for special therapy directed toward the prevention of central nervous system leukemia.

When L-asparaginase is to be used as the sole induction agent for pediatric patients or adults, the recommended dosage regimen is 200 ILL/kg/day intravenously for 28 days.

Etoposide

A recommended dose of etoposide in combination with other approved chemotherapeutic agents ranges from 50 to 100 mg/m$^2$/day on days 1 through 5 to 100 mg/m$^2$/day on days 1, 3 and 5. Etoposide can also be administered in combination with other approved chemotherapeutic drugs in dose ranges from 35 mg/m2/day for 4 days to 50 mg/m$^2$/day for 5 days. Chemotherapy courses are repeated at 3- to 4-week intervals after adequate recovery from any toxicity.

Methotrexate

Methotrexate alone or in combination with steroids can be used initially for induction of remission in acute lymphoblastic leukemia (ALL). More recently corticosteroid therapy, in combination with other antileukemic drugs or in cyclic combinations with methotrexate included, has appeared to produce rapid and effective remissions. When used for induction, methotrexate in doses of 3.3 mg/m$^2$ in combination with 60 mg/m$^2$ of prednisone, given daily, produced remissions in 50% of patients treated, usually within a period of 4 to 6 weeks. Methotrexate in combination with other agents appears to be the drug of choice for securing maintenance of drug-induced remissions.

When remission is achieved and supportive care has produced general clinical improvement, maintenance therapy is initiated, as follows: Methotrexate is administered 2 times weekly either by mouth or intramuscularly in total weekly doses of 30 mg/m$^2$. It has also been given in doses of 2.5 mg/kg intravenously every 14 days. If and when relapse does occur, re-induction of remission can again usually be obtained by repeating the initial induction regimen.

Cytarabine

In the induction therapy of acute non-lymphocytic leukemia, the usual cytarabine dose in combination with other anti-cancer drugs is 100 mg/m2/day by continuous IV infusion (Days 1-7) or 100 mg/m2 IV every 12 hours (Days 1-7).

Imatinib

Imatinib can be administered in the following manner dependent on patient and cancer specifics:

Adults with Ph+CML CP:400 mg/day; Adults with Ph+CML AP or BC:600 mg/day; Pediatrics with Ph+CML CP:340 mg/m$^2$/day; Adults with Ph+ALL:600 mg/day; Pediatrics with Ph+ALL:340 mg/m$^2$/day; Adults with MDS/MPD:400 mg/day; Adults with ASM:100 mg/day or 400 mg/day; Adults with HES/CEL:100 mg/day or 400 mg/day; Adults with DFSP:800 mg/day; Adults with metastatic and/or unresectable GIST:400 mg/day; Adjuvant treatment of adults with GIST:400 mg/day; Patients with mild to moderate hepatic impairment:400 mg/day; Patients with severe hepatic impairment:300 mg/day.

Dasatinib

Chronic phase CML:100 mg once daily. Accelerated phase CML, myeloid or lymphoid blast phase CML, or Ph+ALL:140 mg once daily.

Azacitidine

The recommended starting dose of azacitidine for the first treatment cycle, for all patients regardless of baseline hematology values is 75 mg/m$^2$ daily for 7 days to be administered by subcutaneous (SC) injection or intravenous (IV) infusion. Premedicate for nausea and vomiting. Repeat cycles every 4 weeks. After 2 cycles, may increase dose to 100 mg/m$^2$ if no beneficial effect is seen and no toxicity other than nausea and vomiting has occurred patients should be treated for a minimum of 4 to 6 cycles. Complete or partial response may require additional treatment cycles. Continue treatment as long as the patient continues to benefit. Monitor patients for hematologic response and for renal toxicity; delay or reduce dosage as appropriate.

6-Mercaptopurine (6-MP)

The starting dose of 6-MP in multi-agent combination chemotherapy maintenance regimens is 1.5 to 2.5 mg/kg (50 to 75 mg/m2) as a single daily dose.

Decitabine

There are two regimens for decitabine administration. With either regimen it is recommended that patients be treated for a minimum of 4 cycles; however, a complete or partial response may take longer than 4 cycles.

Treatment Regimen—Option 1

Administer decitabine at a dose of 15 mg/m2 by continuous intravenous infusion over 3 hours repeated every 8 hours for 3 days. Repeat cycle every 6 weeks.

Treatment Regimen—Option 2

Administer decitabine at a dose of 20 mg/m2 by continuous intravenous infusion over 1 hour repeated daily for 5 days. Repeat cycle every 4 weeks. (2.2)

Idarubicin

For induction therapy with idarubicin in adult patients the following dose schedule is recommended: 12 mg/m$^2$ daily for 3 days by slow (10 to 15 min) intravenous injection in combination with cytarabine. The cytarabine may be given as 100 mg/m$^2$ daily by continuous infusion for 7 days or as cytarabine 25 mg/m$^2$ intravenous bolus followed by cytarabine 200 mg/m$^2$ daily for 5 days continuous infusion. In patients with unequivocal evidence of leukemia after the first induction course, a second course may be administered. Administration of the second course should be delayed in patients who experience severe mucositis, until recovery from this toxicity has occurred, and a dose reduction of 25% is recommended. In patients with hepatic and/or renal impairment, a dose reduction of idarubicin should be considered.

Fludarabine

The recommended adult dose of fludarabine phosphate for injection is 25 mg/m$^2$ administered intravenously over a period of approximately 30 minutes daily for five consecutive days. Each 5 day course of treatment should commence every 28 days. Dosage may be decreased or delayed based on evidence of hematologic or nonhematologic toxicity. Physicians should consider delaying or discontinuing the drug if neurotoxicity occurs Thalidomide Thalidomide and its analogues is indicated for the treatment of patients with Multiple myeloma (MM), in combination with dexamethasone. Transfusion-dependent anemia due to low-or intermediate-1-risk myelodysplastic syndromes (MDS) associated with a deletion 5q abnormality with or without additional cytogenetic abnormalities. Mantle cell lymphoma (MCL) whose disease has relapsed or progressed after two prior therapies, one of which included bortezomib.

Recommended thalidomide dosage is as follows:

MM: 25 mg once daily orally on Days 1-21 of repeated 28-day cycles.

MDS: 10 mg once daily.

MCL: 25 mg once daily orally on Days 1-21 of repeated 28-day cycles

Bortezomib

For subcutaneous or intravenous use only The recommended starting dose of bortezomib is 1.3 mg/m² administered either as a 3 to 5 second bolus intravenous injection or subcutaneous injection.

Gemcitabine

Gemcitabine is administered by the intravenous route, since it is extensively metabolized by the gastrointestinal tract. Dose ranges from 1-1.2 g/m² of body surface area according to type of cancer treated.

Paclitaxel

For patients with non-small cell lung carcinoma, the recommended regimen, given every 3 weeks, is paclitaxel administered intravenously over 24 hours at a dose of 135 mg/m² followed by cisplatin, 75 mg/m².

Negative Chemotherapy Side Effects

In some embodiments, methods of the present invention relate to subjects who are or have received a chemotherapeutic regimen associated with one or more negative chemotherapy side effects. In some embodiments, methods of the present invention relate to delay of onset or reduction of one or more of incidence and severity of one or more negative chemotherapy side effects. In some embodiments, negative chemotherapy side effects can include, but are not limited to hair loss, mouth sores, loss of appetite, nausea, vomiting, diarrhea, infections, low blood counts, liver and renal toxicity, neurotoxicity, sun sensitivity, dry itchy skin, skin darkening, mental or mood changes, and allergic reactions. In some embodiments, a negative chemotherapy side effect of low blood counts can result in lowered resistance to infection, fatigue, and easy bruising or bleeding.

ZDHHC9 Inhibition Therapy

The present disclosure provides, among other things, therapeutic regimens that comprise administering ZDHHC9 inhibition therapy to subjects, e.g., to cancer patients. In some embodiments, such cancer patients will be receiving, will have received, and/or will be scheduled to receive one or more chemotherapy regimens. In some embodiments, ZDHHC9 inhibition therapy may delay onset of or reduce one or more of incidence and severity of negative chemotherapy side effects. In some embodiments, ZDHHC9 inhibition therapy may be a treatment for a subject suffering from cancer. In some embodiments, ZDHHC9 inhibition therapy may delay onset of or reduce one or more of incidence and severity of negative chemotherapy side effects in a subject and be a treatment for a subject suffering from cancer.

In general, ZDHHC9 inhibition therapy is any therapeutic modality or regimen whose administration to a subject acts as an inhibitor of ZDHHC9 (i.e., results in reduction in level and/or activity of ZDHHC9). Those skilled in the art will appreciate that, in some embodiments, a particular therapeutic modality or regimen may be considered to be ZDHHC9 inhibition therapy if it has been demonstrated to achieve statistically significant ZDHHC9 inhibition when administered to a relevant population; demonstration that ZDHHC9 inhibition actually occurs, or occurs to a particular degree in each or any specific individual to whom the therapy is administered is not required.

In some embodiments, one or more doses of (and in some embodiments all doses of) ZDHHC9 inhibition therapy is/are administered prior to initiation of a chemotherapeutic regimen. In some embodiments, one or more doses of (and in some embodiments all doses of) ZDHHC9 inhibition therapy is/are administered substantially concurrently with one or more chemotherapy doses in a chemotherapeutic regimen. In some embodiments, one or more doses of (and in some embodiments all doses of) ZDHHC9 inhibition therapy is/are administered after one or more chemotherapy doses in a chemotherapeutic regimen.

In some embodiments, one or more doses of (and in some embodiments all doses of) ZDHHC9 inhibition therapy is/are administered prior to development of one or more negative chemotherapy side effects. In some embodiments, one or more doses of (and in some embodiments all doses of) ZDHHC9 inhibition therapy is administered after the development of one or more negative chemotherapy side effects.

In some embodiments, ZDHHC9 inhibition therapy reduces palmitoylation of NRAS. In some embodiments, ZDHHC9 inhibition therapy reduces translocation of NRAS to the plasma membrane.

In some embodiments, cancer patients to whom ZDHHC9 inhibition therapy is administered in accordance with the present invention are suffering from or susceptible to one or more cancers as discussed above.

Combination Therapy

In some embodiments, ZDHHC9 inhibition therapy may be administered in combination with one or more other anti-cancer therapies including, for example administration of chemotherapeutic regimens, immunomodulatory agents, anti-tumor antagonist agents (e.g., anti-tumor antibodies), radiation therapy, high-frequency ultrasound therapy, surgery, other etc.

Alternatively or additionally, in some embodiments, ZDHHC9 inhibition therapy may be administered in combination with one or more palliative (e.g., pain relieving, anti-nausea, anti-emesis, etc) therapies, particularly when the palliative therapy or therapies relieves one or more symptoms known to be associated with the relevant cancer, or with another disease, disorder or condition to which a particular cancer patient is susceptible or from which the particular cancer patient is suffering.

Alternatively or additionally, in some embodiments, ZDHHC9 inhibition therapy may be administered in combination with one or more other therapies that achieves inhibition of palmitoylation, e.g., of RAS and/or NRAS.

In some embodiments, one or more therapies used in combination in accordance with the present invention are administered according to a protocol or dosing regimen for which it/they is/are approved for individual use. For example, in some embodiments, one or more utilized agents is administered according to a dosing regimen approved by a regulatory authority such as the United States Food and Drug Administration (FDA) and/or the European Medicines Agency (EMEA), e.g., for the relevant indication. In some embodiments, however, combination (e.g., in the context of or in addition to ZDHHC9 inhibition therapy) permits an therapy to be administered according to a protocol or dosing regimen that involves one or more lower and/or less frequent doses, and/or a reduced number of cycles as compared with that utilized when the agent is administered without provided staggered therapy. Alternatively or additionally, in some embodiments, an appropriate dosing regimen involves higher and/or more frequent doses, and/or an increased number of cycles as compared with that utilized when the therapy is administered other than in the relevant combination therapy (e.g., not in combination with ZDHHC9 inhibition therapy).

In some embodiments, one or more doses of agents administered in combination are administered at the same time; in some such embodiments, agents may be administered in the same composition. More commonly, however, agents are administered in different compositions and/or at different times.

In some embodiments, where two or more active agents are utilized in accordance with the present invention, such agents can be administered simultaneously or sequentially. In some embodiments, administration of one agent is specifically timed relative to administration of another agent. For example, in some embodiments, a first agent is administered so that a particular effect is observed (or expected to be observed, for example based on population studies showing a correlation between a given dosing regimen and the particular effect of interest).

In some embodiments, desired relative dosing regimens for agents administered in combination may be assessed or determined empirically, for example using ex vivo, in vivo and/or in vitro models; in some embodiments, such assessment or empirical determination is made in vivo, in a patient population (e.g., so that a correlation is established), or alternatively in a particular patient of interest.

Formulations

Therapeutic compositions for use in accordance with the present invention may be prepared for storage and/or delivery using any of a variety of techniques and/or technologies known and/or available to those skilled in the art. In general, dosing and administration according to the present invention utilizes therapeutic compositions, which comprise an active agent (e.g., having a desired degree of purity) combined with one or more physiologically acceptable carriers, excipients or stabilizers in any of a variety of forms. Such forms include, for example, liquid, semi-solid and solid dosage forms, such as liquids, gels, tablets, capsules, powders, patches, suppositories, etc. In some embodiments, a preferred form may depend on the intended mode of administration and/or therapeutic application.

Identification and/or Characterization of ZDHHC9 Inhibitors

Model Systems

In some embodiments of the present invention a model system can be used to identify and/or characterize ZDHHC9 inhibitors. In some embodiments, a model system comprises NRAS. In some embodiments, NRAS palmitoylation in the model system serves as a proxy of ZDHHC9 activity.

In some embodiments, a model system is in vitro. In some embodiments, a model system is ex vivo. In some embodiments, a model system is in vivo.

In some embodiments, a model system is or comprises a cultured cell. In some embodiments, a model system is or comprises a cultured cell engineered to express exogenous ZDHHC9. In some embodiments, a cultured cell model system can be prokaryotic or eukaryotic. In some embodiments, a eukaryotic cultured cell model system can be, but is not limited to, human, rodent, insect, or plant cells. In some embodiments, a model system is or comprises BaF3 cells. In some embodiments, a model system is or comprises bone marrow cells.

In some embodiments, a model system is or comprises an organism. In some embodiments, an animal model system can be, but is not limited to, insects, rodents, amphibians, nematodes, and non-human primates. In some embodiments, an organismal model system can be engineered to express exogenous ZDHHC9.

In some embodiments, an inhibitor may be an agent that reduces the presence, level, or activity of ZDHHC9 or an active form thereof. In some embodiments, reduction of presence, level, or activity can result from reduction of transcription or reduction of translation. In some embodiments, an inhibitor may be a test agent as described herein.

Test Agents

In general, a test agent is any entity, condition or event whose effect on ZDHHC9 can be assessed in accordance with the present disclosure.

In some embodiments test agents used in the present invention can be or comprise a polypeptide, polynucleotide, lipid, carbohydrate, large molecule, small molecule, metal, or other mode of therapeutic agent.

In some embodiments, a polypeptide test agent can be or comprise a peptide inhibitor. In some embodiments, a polypeptide test agent can be or comprise a competitive peptide inhibitor. In some embodiments, a polypeptide test agent can be or comprise an allosteric peptide inhibitor.

In some embodiments, a polypeptide test agent can be or comprise an antibody agent. In some embodiments, a polypeptide test agent can be or comprise an anti-ZDHHC9 antibody agent.

In some embodiments, a polynucleotide test agent can be or comprise an antisense polynucleotide complementary to a ZDHHC9 coding or regulatory sequence. In some embodiments, a polynucleotide test agent can be or comprise an siRNA that targets or otherwise impacts a ZDHHC9 coding or regulatory sequence. In some embodiments, a polynucleotide test agent can be or comprise a miRNA that targets or otherwise impacts a ZDHHC9 coding or regulatory sequence.

In some embodiments, a test agent may be or comprise a gene editing agent whose activity targets or otherwise impacts a ZDHHC9 coding or regulatory sequence.

In some embodiments, a small molecule test agent can be or comprise a reversible ZDHHC9 inhibitor. In some embodiments, a small molecule test agent can be or comprise an irreversible ZDHHC9 inhibitor. In some embodiments, a small molecule test agent can be or comprise a competitive ZDHHC9 inhibitor. In some embodiments, a small molecule test agent can be or comprise an allosteric ZDHHC9 inhibitor.

Characterization

In some embodiments, a test agent is deemed to be a ZDHHC9 inhibitor if, when assessed as described herein, its presence correlates with a reduction in ZDHHC9 level and/or activity. In some embodiments, such reduction is statistically significant. In some embodiments, such reduction is assessed relative to an appropriate control (e.g., absence of the test agent and/or presence of a known inhibitor).

In some embodiments, such reduction is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, 9 at least about 5%, at least about 96%, at least about 97%, at least about 98%, at least about 99% or more.

In some embodiments, such reduction is at least about 2 fold, at least about 3 fold, at least about 4 fold, about 5 fold, about 6 fold, about 7 fold, about 8 fold, about 9 fold, about 10 fold, about 20 fold, about 30 fold, about 40 fold, about 50 fold, about 60 fold, about 70 fold, about 80 fold, about 90 fold, about 100 fold, about 200 fold, about 300 fold, about 400 fold, about 500 fold, about 600 fold, about 700 fold, about 800 fold, about 900 fold, about 100 fold, about 10,000 fold, about 1000,000 fold, or more.

In some embodiments, a test agent is deemed to be a ZDHHC9 inhibitor if it competes with a known inhibitor to achieve inhibition of ZDHHC9.

EXEMPLIFICATION

The following examples are provided so as to describe to those of ordinary skill in the art how to make and use methods and compositions of the invention, and are not intended to limit the scope of what the inventors regard as their invention.

Example 1

Materials and Methods

The present Example describes those materials and methods used in the generation of the foregoing Examples.

Mouse strains

The knockout (KO) mouse strain of X chromosome-linked Zdhhc9 gene (Lexicon Genetics Pharmaceuticals, Taconic Farms, Germantown, N.Y.) was maintained in a mixed 129/SvEvBrd and C57BL/6 background. $Nras^{LSL-G12D/+}$ conditional knock-in mice[21] (Taconic Farms) were maintained in a C57BL/6 background as described.[22] Mx1-Cre transgenic mice (Model Animal Research Center of Nanjing University, Nanjing, China) were used to conditionally switch on $Nras^{G12D}$ expression in hematopoietic cells. Mx1-Cre; $Nras^{G12D/G12D}$;$Zdhhc9^{KO}$ and Mx1-Cre; $Nras^{G12D/G12D}$;$Zdhhc9^{WT}$ triple mutant mice were generated by the following cross breeding strategy: female $Zdhhc9^{-/-}$ mice were crossed with male Mx1-Cre mice to generate Mx1-Cre;$Zdhhc9^{+/-}$ female mice; Female Mx1-Cre;$Zdhhc9^{-/-}$ mice were crossed with male $Nras^{LSL-G12D/+}$ mice to produce Mx1-Cre;$Nras^{LSL-G12D/+}$; $Zdhhc9^{+/-}$ and Mx1-Cre; $Nras^{LSL-G12D/+}$; $Zdhhc9^{-/y}$ mice. By inbreeding with these mice, Mx1-Cre;$Nras^{LSL-G12D/LSL-G12D}$;$Zdhhc9^{KO}$ offspring were generated as well as the Mx1-Cre; $Nras^{LSL-G12D/LSL-G12D}$;$Zdhhc9^{WT}$ control. C57BL/6.SJL (CD45.1) mice (Jackson Laboratory, Bar Harbor, Me.) and C57BL/6 (CD45.2) mice (Shanghai SLAC Laboratory Animal Co.Ltd, Shanghai, China) were used in bone marrow transplantation (BMT) experiments. Standard methods were used for mice grouping. All procedures were conducted with the ethical approval of the Animal Care & Welfare Committee of Shanghai Jiao Tong University School of Medicine.

Induction of myeloproliferative neoplasia in mice with conditional knock-in alleles of oncogenic Nras Four-week-old Mx1-Cre;$Nras^{G12D/G12D}$;$Zdhhc9^{KO}$ and Mx1-Cre; $Nras^{G12D/G12D}$;$Zdhhc9^{WT}$ mice were intraperitoneally injected with 250 µg polyinosinic-polycytidylic acid (pIpC, Sigma, St. Louis, Mo.) twice at a one-day interval to induce expression of Mx1 promoter-controlled Cre recombinase in hematopoietic tissues as described.[23]

Induction of acute T-cell lymphoblastic leukemia (T-ALL) using mice with conditional knock-in alleles of oncogenic Nras The induction of T-ALL using mice with conditional knock-in alleles of oncogenic Nras was performed as described.[23] Briefly, $2 \times 10^5$ bone marrow (BM) cells from pIpC-treated Mx1-Cre;$Nras^{G12D/G12D}$;$Zdhhc9^{KO}$ or Mx1-Cre;$Nras^{G12D/G12D}$;$Zdhhc9^{WT}$ donor mice (CD45.2) were mixed with an equal number of those from C57BL/6 wild-type donors (CD45.1). The cells were then intravenously injected into lethally irradiated (two doses of 350 cGy at a 4-hour interval) C57BL/6 wild-type recipients (CD45.1).

Hematological and Immunophenotypic Analysis

Peripheral blood was obtained from mice by tail bleeding. White blood cell (WBC), red blood cell (RBC), platelet (PLT) and hemoglobin (Hb) counts were tested using a pocH-100iV Diff hematology analyzer (Sysmex Corporation, Kobe, Japan). After lysing the RBC, peripheral blood, BM, spleen or thymus cells were stained with conjugated antibodies to specific surface antigens as follows. CD150 (Q38-480), CD48 (HM48-1), c-kit (2B8), Sca-1 (D7), Mac-1 (M1/70), Gr-1 (RB6-8C5), CD19 (1D3), B220 (RA3-6B2), CD3 (145-2C11), CD4 (GK1.5), CD8 (53-6.7), CD44 (IM7), CD25 (3C7), CD45.1 (A20), CD45.2 (104) and Biotin Mouse Lineage Panel (559971) were all purchased from BD Pharmingen (San Diego, Calif.). All fluorescence-activated cell sorter (FACS) analyses were performed on an LSR II system (BD Biosciences, San Jose, Calif.). Data were analyzed with FlowJo software (Tree Star, San Carlos, Calif.). For cell sorting experiments, B cells ($CD19^+$/$B220^+$), T cells ($CD3^+$) or myeloid cells ($Mac-1^+$/$Gr-1^+$) were purified from wild-type BM cells by a MoFlo high-speed cell sorter (Dako-Cytomation, Carpinteria, Calif.).

5-Fluorouracil Treatment Experiment

For single dose 5-Fluorouracil (5-FU) treatment, 8-week-old mice were intraperitoneally injected with 5-FU (150 mg/kg) and monitored every three days until blood counts recovered. For serial 5-FU treatment experiment, 5-FU was administered weekly at a dose of 150 mg/kg intraperitoneally to mice until the first mouse died. Sequential blood counts were obtained every three days, and survival was monitored closely.

Colony Forming Unit Assay and Confocal Microscopy Imaging

For mouse BM colony-forming unit (CFU) assay, $2 \times 10^4$ whole BM cells were isolated from 8-week-old $Zdhhc9^{WT}$ or $Zdhhc9^{KO}$ mice and plated in MethoCult M3434 methylcellulose medium (StemCell Technologies, Vancouver, Canada). Colonies were identified and counted at day 7 or day 12 according to the manufacturer's instruction. For NRAS-transformed CFU assay, BM cells were isolated from mice pretreated with 5-FU (250 mg/kg), and transduced with GFP-fused $NRAS^{G12D}$ ($GFP-NRAS^{G12D}$) or $GFP-NRAS^{G12D/C181S}$ retroviruses as previously described.[9] After infection for 2 days in vitro, $1 \times 10^4$ $GFP^+$ BM cells were sorted and plated in cytokine-free medium (MethoCult M3231). A week later, colonies were scored and imaged with an inverted microscope (Nikon Eclipse Ti, Tokyo, Japan) using a 20-fold objective lens at room temperature (original magnification×200). Subsequently, cells were recovered from the methylcellulose medium and cultured in liquid medium for live imaging by a confocal laser scanning microscope (Leica TCS SP8, Wetzlar, Germany) with a 63-fold oil-immersion objective lens at 37° C. and 5% $CO_2$ condition (original magnification×630). The captured images were processed by NIH ImageJ software.

Palmitoylation Assay

Palmitoylation of RAS proteins were determined by the acyl-biotinyl exchange (ABE) method as described previously with modifications.[24] Briefly, 500 µg membrane proteins extracted from each sample with MemPER Plus Membrane Protein Extraction Kit (Pierce, Rockford, Ill.) were used for ABE assay. Protein concentration was measured using the Micro BCA protein assay (Pierce). To denature proteins, membrane solutions were buffer-exchanged with high concentration of SDS Buffer (4% SDS, 50 mM Tris-HCl, 5 mM EDTA, pH 7.4) by using Zeba Spin Desalting Columns (Pierce), and then incubated at 50° C. for 10 minutes. To reduce disulfide bonds, samples were treated with 10 mM tris(2-carboxyethyl)phosphine hydrochloride (TECP-HCl, pH 7.4) (Sigma) for 30 minutes. Samples were then desalted by Zeba spin columns according to the manufacturer's instruction. All exposed thiol groups were blocked by N-ethylmaleimide (NEM) Buffer (100 mM NEM, 1% SDS, 50 mM Tris-HCl, pH 7.2) at room temperature (RT) for 3 hours with agitation. After another Zeba desalting procedure to remove excess NEM, samples were divided equally into two portions. One portion was diluted with 5 volumes of hydroxylamine (HA, Sigma)-containing Buffer (1 M HA, 0.2% Triton X-100, pH 7.2) to selectively cleave the thioester bond of palmitoylated proteins. And the other portion was mixed with 5 volumes of HA-free Buffer (50 mM Tris, 0.2% Triton X-100, pH 7.2) as a negative control. Both portions were gently rotated at RT for 1 hour. After removing excess HA by Zeba desalting columns, each portion of samples was treated with 1-Biotinamido-4-[4'-(maleimidomethyl)cyclohexanecarboxamido]butane (Biotin-BMCC) (Pierce), a sulfhydryl-reactive biotinylation reagent, in buffer (200 µM Biotin-BMCC, 150 mM NaCl, 50 mM Tris-HCl, 5 mM EDTA, pH 7.2) at RT for 1 hour to label all newly exposed thiol groups. Excess Biotin-BMCC was then removed by a final Zeba desalting procedure. Biotinylated membrane proteins were precipitated with streptavidin-agarose beads (S1638, Sigma) at 4° C. overnight. After 4-time washes with lysis buffer (150 mM NaCl, 50 mM Tris-HCl, 5 mM EDTA, pH 7.4), biotinylated proteins were eluted by boiling with 5×SDS-PAGE loading buffer (250 mM Tris-HCl, 10% SDS, 0.5% Bromophenol blue, 50% glycerol, 25% β-mercaptoethanol, pH 6.8) for 5 minutes and ready for western blotting. 5% samples collected before precipitation were also kept as an input control.

Western Blotting Analysis

Western blot analysis was performed as previously described.[25] Anti-ZDHHC9 rabbit polyclonal antibody (HPA031814, Sigma), anti-RAS RAS10 monoclonal antibody (05-516, Millipore, Billerica, Mass.) and anti-β-actin (A1978, Sigma) were used as primary antibodies. The western blot images were detected with the FluorChem M System (ProteinSimple, Santa Clara, Calif.), and quantified by NIH ImageJ software.

Polymerase Chain Reaction (PCR)

For mouse strain genotyping, tail DNAs were extracted by Wizard Genomic DNA Purification Kit (Promega, Madison, Mich.) and detected by genomic PCR using specific primers. For reverse transcription PCR (RT-PCR), total RNAs were isolated from RBC-lysed cells using TRizol reagent (Invitrogen) and reversely transcribed by MMLV reverse transcriptase (Invitrogen) per manufacturer's instruction. Real-time quantitative PCR (qPCR) was performed with GoTaq° qPCR System (Promega) for measuring relative mRNA expression level of Zdhhc genes with the comparative Threshold Cycle ($C_T$) method. Briefly, the expression of specific Zdhhc gene was normalized by subtracting the $C_T$ value of endogenous Gapdh housekeeper gene to the individual gene ($\Delta C_T = C_T$(Zdhhc gene)-$C_T$ (Gapdh)). The value of relative mRNA expression level was calculated with the formula $2^{\Delta C_T}$. Semi-quantitative RT-PCR was also performed to determine mRNA expression level of Zdhhc9 gene. The primers used above are all listed in Table 1.

Statistical Analysis

For mean comparison between two groups, the unpaired Student's t-test was used for normal distribution with equal variance; otherwise, the non-parametric Mann-Witney U tests were used. For survival analysis, the Kaplan-Meier survival curves were plotted and P values were calculated by log-rank test. Sample sizes were chosen by standard methods to ensure adequate power and no statistical method was used to pre-estimate the sample size. No randomization and blinding were used for animal studies. The data were presented as mean±SEM (standard error of the mean). The variations of data were calculated from at least three independent experiments. Graphpad Prism 6 software was used for statistical data analysis.

Example 2

ZDHHC9 Inactivation Significantly Reduces Palmitoylation of RAS in Bone Marrow Cells.

Figure 1B:
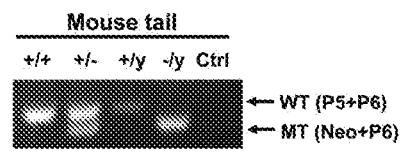

This Example demonstrates that the inactivation of ZDHHC9 reduces palmitoylation of RAS. A Zdhhc9-knockout)(Zdhhc9$^{KO}$ mouse strain was generated by using the strategy depicted in FIG. 1a. The wild-type allele of Zdhhc9 was mutated by replacing the translation start site in exon 2 with an artificial selective cassette of LacZ/Neo. Genotyping of mouse-tail genomic DNA shows that heterozygote mouse contains both wild type and mutant alleles of Zdhhc9, while mutant male mouse contains only the Zdhhc9 knockout allele (FIG. 1b).

Figure 1C:
Figure 1D:
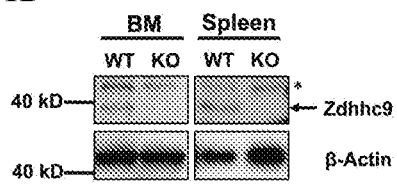
Figure 1E:
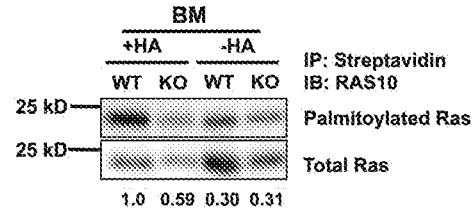

To study the effect of Zdhhc9 inactivation in a hematopoietic system, it was first confirmed that the expression of the Zdhhc9 transcripts was undetectable in hematopoietic tissues from Zdhhc9$^{KO}$ mice (FIG. 1c). Western blot analysis shows that the Zdhhc9 protein was not expressed in Zdhhc9$^{KO}$ mouse BM and spleen (FIG. 1d). To determine whether Zdhhc9 is a bona fide PAT for Ras palmitoylation in vivo, the acyl-biotinyl exchange (ABE) assay was performed to assess the palmitoylation status of Ras in BM cells from Zdhhc9$^{KO}$ mice and wild-type control mice. Results showed that the palmitoylation level of Ras is significantly decreased, yet not abolished, in BM of Zdhhc9$^{KO}$ mice, compared to their wild-type counterparts (FIG. 1e). This result demonstrates that Zdhhc9 is a Ras PAT in vivo, but suggests there are other Ras PATs.

Example 3

ZDHHC9 Inactivation Does not Affect Normal Hematopoiesis Under Homeostatic Conditions.

This Example demonstrates that ZDHHC9 is dispensable in normal hematopoiesis under steady-state conditions. Zdhhc9$^{KO}$ mice were born at the expected Mendelian ratio (data not shown). The body weight of adult Zdhhc9-deficient mice is similar to the wild-type control mice (FIG. 2b). During a follow-up period of two years, Zdhhc9$^{KO}$ mice were viable, fertile and exhibited no noticeable abnormalities compared to their wild-type littermates (data not shown).

As Zdhhc9 inactivation abrogates palmitoylation of the endogenous Ras proteins in Zdhhc9-deficient BM cells, the role of Zdhhc9 in normal hematopoiesis in vivo was evaluated. The absolute numbers of leukocytes, erythrocytes, platelets and hemoglobin level in peripheral blood of Zdhhc9$^{KO}$ mice were similar to that of wild-type control mice in the 6 month observation period (FIG. 2a). The sizes of hematopoietic tissues, liver, spleen and thymus, were not affected by Zdhhc9 deficiency (FIG. 2b). The absolute numbers of cells in BM and spleen were also similar between Zdhhc9$^{KO}$ mice and the wild-type control mice (FIG. 2c).

It was next determined whether Zdhhc9 deficiency has an effect on hematopoietic stem cells (HSC). We examined the frequencies of HSC in the lineage⁻, Sca1⁺, c-Kit⁺ population of cells (LSK cells), and long-term SLAM⁺ HSC (CD150⁺, CD48⁻, Lineage⁻, Sca1⁺, c-Kit⁺; LT-HSC), and found that there are no apparent differences in both populations of HSCs between Zdhhc9$^{KO}$ and Zdhhc9$^{WT}$ mice (FIG. 2d). Consistently, no significant differences were found in B cells (CD19⁺ and B220⁺), myeloid cells (Mac-1⁺ and Gr-1⁺), or T cells (CD3⁺) from BM of both groups (FIG. 2d).

To assess the clonogenic potential of hematopoietic stem cells and progenitors (HSCPs), BM cells were isolated from Zdhhc9$^{KO}$ and Zdhhc9$^{WT}$ mice to perform the colony-forming unit (CFU) assays. There were no apparent differences between Zdhhc9$^{KO}$ and Zdhhc9$^{WT}$ mice in CFUs or BFUs (FIG. 2e), demonstrating that Zdhhc9 deficiency does not affect the clonogenicity of HSPCs.

Example 4

ZDHHC9 Inactivation Resists Hematopoietic Stress by Fluoracil

Figure 3A:
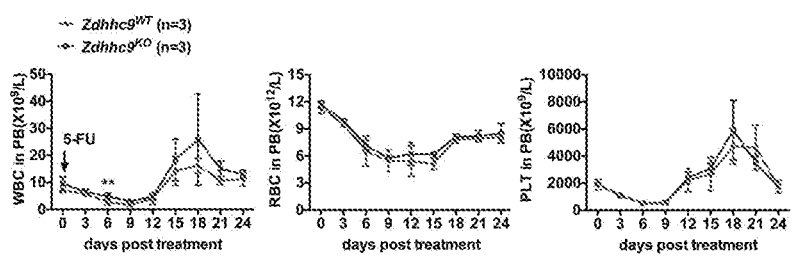
FIGS. 3A-3C demonstrate that Zdhhc9 inactivation moderately resists to hematopoietic stress by 5-FU. Data are representative of 3 independent experiments. *P<0.05, **P<0.01.
Figure 3B:
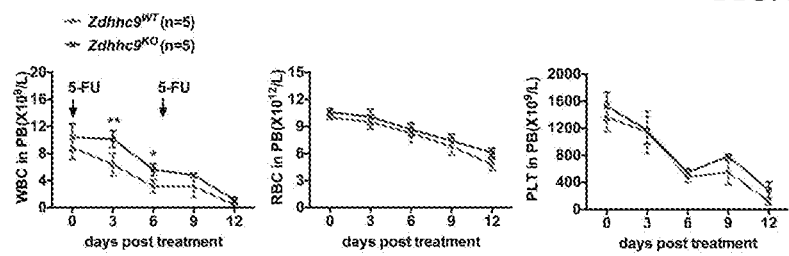
Figure 3C:
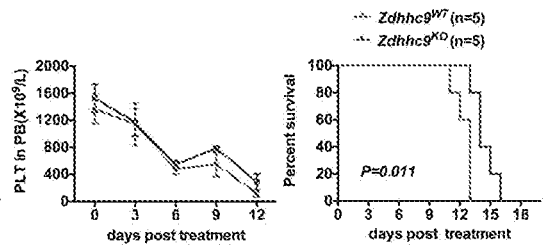

This Example demonstrates that ZDHHC9 may delay onset or reduce incidence or severity of negative chemotherapy side effects. To examine the biological functions of Zdhhc9 in hematopoietic cells under stress conditions, Zdhhc9$^{KO}$ and Zdhhc9$^{WT}$ mice were treated with 5-FU. Recovery of peripheral WBC was slightly quicker in single dose 5-FU treated Zdhhc9$^{KO}$ mice than that of Zdhhc9$^{WT}$ mice (FIG. 3a). The reduction of peripheral WBC counts and death of 2 doses 5-FU treated Zdhhc9 deficient mice were also moderately but significantly slower than that of wild-type mice (FIG. 3b and c).

Example 5

ZDHHC9 Inactivation Inhibits Oncogenic NRAS Plasma Membrane Translocation and Cellular Transformation These present Example demonstrates that ZDHHC9 inactivation inhibits oncogenic NRAS plasma translocation and cellular transformation.

To determine the effect of Zdhhc9 inactivation on RAS localization and cellular transformation in hematopoietic cells, oncogenic NRAS (NRAS$^{G12D}$) was transduced into Zdhhc9$^{WT}$ or Zdhhc9$^{KO}$ BM cells by a retroviral vector and performed a colony-forming assay using cytokine-free methylcellulose medium.

Figure 4A:
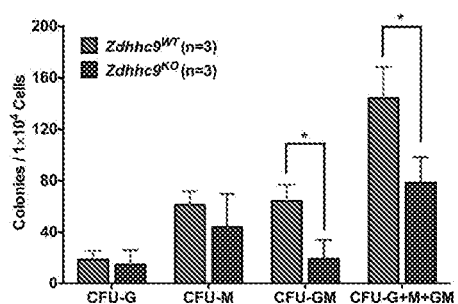
FIGS. 4A-4D demonstrate that Zdhhc9 inactivation inhibits the activity of NRAS$^{G12D}$ to transform BM cells, as well as its palmitoylation and plasma membrane translocation. Data are representative of 3 independent experiments. *P<0.05.
Figure 4B:
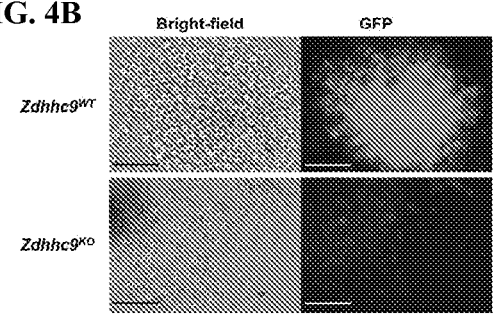
Figure 4C:
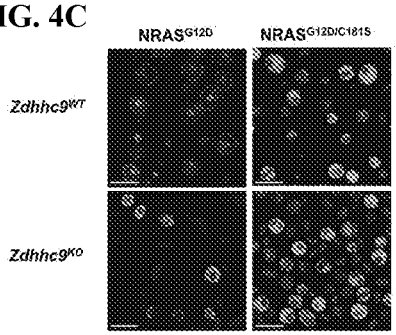
Figure 4D:
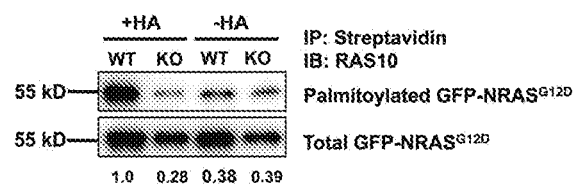

Zdhhc9 inactivation significantly reduced overall CFU numbers, especially CFU-GM, indicating that the oncogenic transformation ability of NRAS$^{G12D}$ is abrogated in Zdhhc9$^{KO}$ BM cells (FIG. 4a). The morphology of the colonies formed by BM cells expressing GFP-fused NRAS$^{G12D}$ was also distinct between two groups (FIG. 4b). Consistently, confocal microscope images of the GFP-NRAS$^{G12D}$ transduced BM cells show that the plasma membrane localization of the GFP-NRAS$^{G12D}$ protein is reduced in the absence of Zdhhc9, resembling the status in the control cells expressing palmitoylation mutant GFP-NRAS$^{G12D/C181S}$ (FIG. 4c). Similar to the result shown in FIG. 1e, the palmitoylation level of the ectopically expressed oncogenic NRAS is reduced in Zdhhc9$^{KO}$ cells recovered from colony-forming assay as compared to that of wild-type control cells (FIG. 4d).

Example 6

ZDHHC9 Inactivation Ameliorates Leukemogenesis by Oncogenic Nras Expressed from the Endogenous Locus The present Example demonstrates that ZDHHC9 plays an important role in leukemogenesis induced by oncogenic NRAS.

RAS mutations are common in human cancers, including hematological malignances. They have been found in about 11% of adult T cell acute lymphocytic leukemia (T-ALL).[26] Especially in early T-cell precursor ALL, mutations in genes involved in RAS signaling occur in approximately 2/3 cases, including 19% NRAS and 3% KRAS mutations.[5] Somatic RAS mutations, predominantly NRAS mutations, are also found in 25-30% of juvenile myelomonocytic leukemia (JMML),[27] >20% of chronic myelomonocytic leukemia (CMML),[28] and 20-25% of acute myeloid leukemia (AML) patients.[29]

Figure 5A:
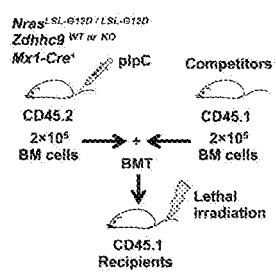
FIGS. 5A-5F demonstrate that Zdhhc9 inactivation significantly suppresses the Nras$^{G12D/G12D}$-induced T-ALL and myeloproliferative neoplasia.
Figure 5B:
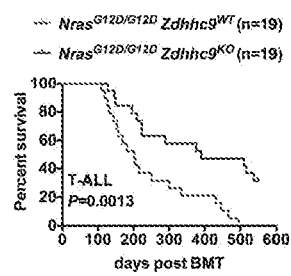
Figure 5C:
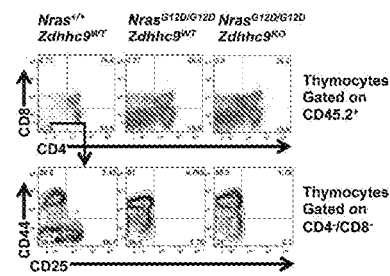
Figure 7:
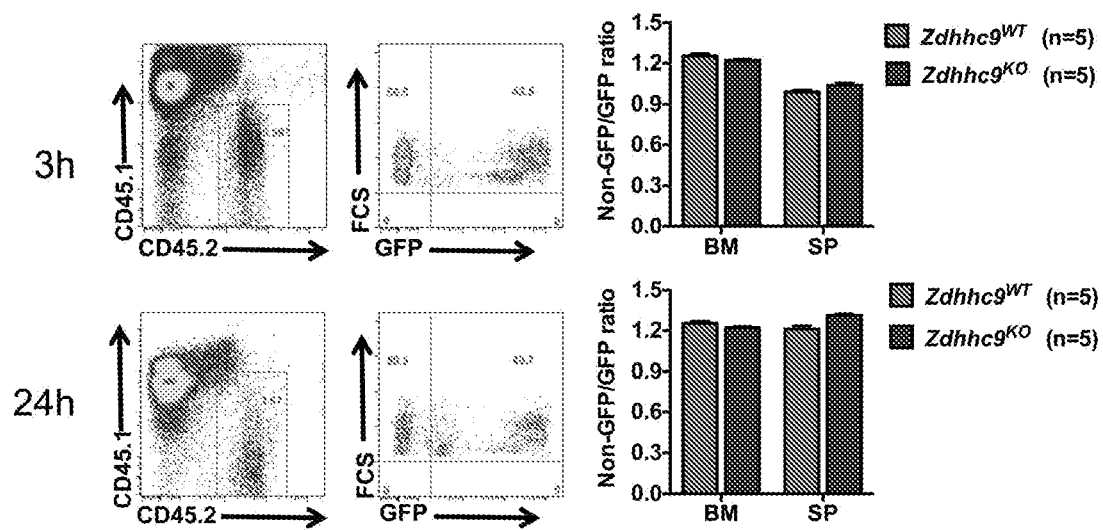
FIG. 7 depicts a homing assay which shows that Zdhhc9 deficiency does not affect the homing ability of bone marrow (BM) cells. Each lethally irradiated CD45.1 recipient mouse was intravenously injected with 5×10$^6$ whole BM cells from Zdhhc9$^{WT}$ (n=4) or Zdhhc9$^{KO}$ (n=4) mice (CD45.2) and equal amount of competitor BM cells from Actb-GFP transgenic mice in C57BL/6 background (CD45.2). 3 or 24 hours after the transplantation (n=5 recipients for each genotype at individual time point), CD45.2$^+$ donor cells from the recipient mice were quantified by FACS analysis. The ratio of non-GFP and GFP cells represents the relative homing activity of Zdhhc9$^{WT}$ or Zdhhc9$^{KO}$ cells compared to normal competitor cells. The results are presented as mean±SEM.

To assess the role of Zdhhc9 in the pathogenesis of T-ALL induced by oncogenic Nras, a BMT mouse model, depicted in FIG. 5a, was established. Hematopoietic cell homing assay showed that there was no difference in homing ability of BM cells between Zdhhc9$^{KO}$ and wild-type mice (FIG. 7). By monitoring the percentage of CD45.2⁺ donor cells and their T-cell surface markers in peripheral blood of recipient mice, we followed up the leukemia development for approximately 560 days. All Nras$^{G12D/G12D}$;Zdhhc9$^{WT}$ recipient mice succumbed to T-ALL, whereas less than 70% of Nras$^{G12D/G12D}$;Zdhhc9$^{KO}$ recipient mice developed the disease, with a slower progression (FIG. 5b). The median survival time was 202 and 390 days for Nras$^{G12D/G12D}$;Zdhhc9$^{WT}$ recipients and Nras$^{G12D/G12D}$;Zdhhc9$^{KO}$ recipients, respectively (P=0.0013, FIG. 5b). The FACS analysis of thymocytes from moribund mice demonstrated that both Zdhhc9$^{WT}$ and Zdhhc9$^{KO}$ mice succumbed to T-ALL (FIG. 5c).

Figure 5D:
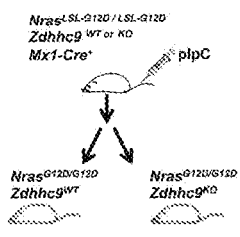
Figure 5E:
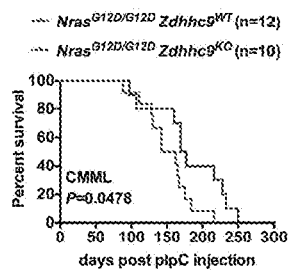
Figure 5F:
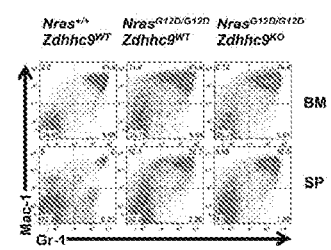

Meanwhile, oncogenic Nras was activated in both Mx1-Cre;Nras$^{LSL-G12D/LSL-G12D}$; Zdhhc9$^{KO}$ and Mx1-Cre;Nras$^{LSL-G12D/LSL-G12D}$; Zdhhc9$^{WT}$ mice by pIpC injection (FIG. 5d). Zdhhc9 inactivation significantly slowed the development of myeloid leukemia and led to an improvement in overall survival of mice (FIG. 5e), though CMML-like disease was developed in both groups, manifested by elevated white blood cell counts, splenomegaly, and myeloid infiltration of BM and spleen (FIG. 5f). The median survival was 152 vs. 173 days for Nras$^{G12D/G12D}$; Zdhhc9$^{WT}$ and Nras$^{G12D/G12D}$; Zdhhc9$^{KO}$ mice respectively (P=0.0478).

Example 7

Differential Expression of Zdhhc Family Genes in Different Hematopoietic Cell Lineages and Changes of Zdhhc Family Gene Expression in Nras Leukemia Cells The present example demonstrates that there is a positive feedback loop between the expression of Zdhhc9 and function of oncogenic NRAS.

Figure 6A:
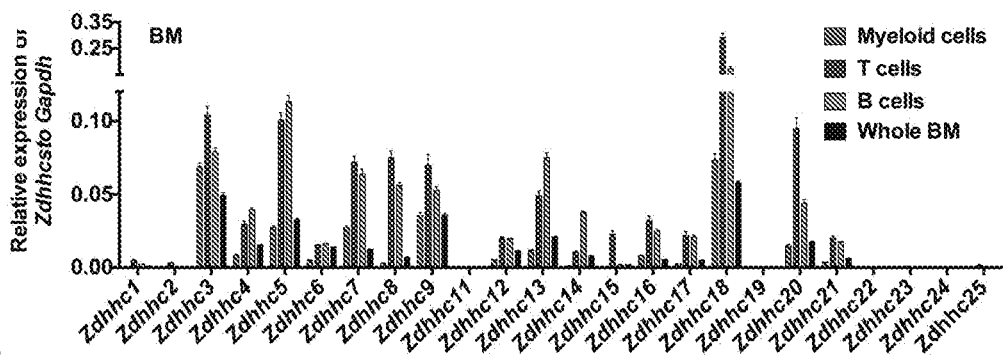
FIGS. 6A-6C present gene expression profiling of Zdhhc family genes in BM cells under the physiological and pathological conditions. Data are representative of 3 independent experiments.

Although Zdhhc9 inactivation could mitigate the leukemia progress, it can't completely eliminate the leukemogeic potential of oncogenic Nras. Besides, Zdhhc9 inactivation exerts different impact on the development of T-ALL vs. CMML. Because Zdhhc9 belongs to a large gene family, compensation effects may be present under both physiological and pathological conditions. To test this possibility, different hematopoietic cell lineages were isolated and sorted from wild-type BM cells by FACS and the mRNA expression of Zdhhc gene family members was examined using RT-qPCR assay. A majority of Zdhhc genes, including Zdhhc9 subfamily (Zdhhc 5/8/9/14/18), are expressed at higher levels in T/B-lymphocytes than that in myeloid cells (FIG. 6a). This result suggests that lymphocytes rely more on protein palmitoylation than that of myeloid cells, which may account, at least partially, the more severe phenotype of Zdhhc9 inactivation in Nras-induced T-ALL compared to that of CMML.

Figure 6B:
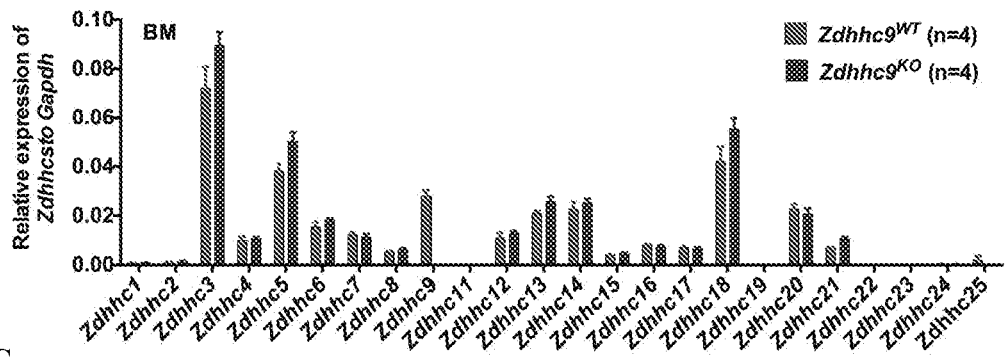

The expression profiles of Zdhhc genes in BM cells from Zdhhc9 and Zdhhc9$^{KO}$ mice were compared. FIG. 6b shows that the expression pattern of Zdhhc genes other than Zdhhc9 in Zdhhc9$^{KO}$ BM cells are similar to those in the wild-type control, indicating that there is no compensatory expression of other Zdhhc genes in the absence of Zdhhc9 under physiological condition.

Figure 6C:
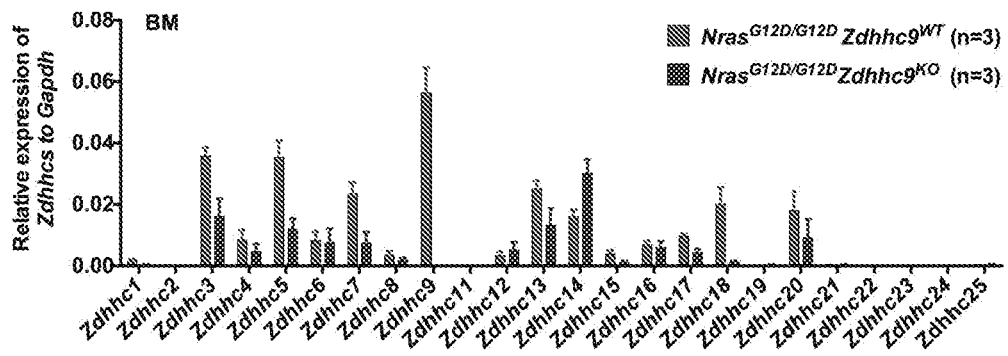

The expression of Zdhhc genes in BM cells from Mx1-Cre;Nras$^{G12D/G12D}$;Zdhhc9$^{WT}$ and Mx1-Cre;Nras$^{G12D/G12D}$;Zdhhc9$^{KO}$ mice that were treated with 3 doses of pIpC 2 months prior to the experiment were also compared (FIG. 6c). The expression of Zdhhc9 in the wild-type BM cells was markedly elevated relative to the rest family members when oncogenic Nras was presence.

Interestingly, in the absence of Zdhhc9, oncogenic Nras reduces the expression levels of majority of Zdhhc genes, while increases the Zdhhc14 expression. Zdhhc14 is the closest homolog of Zdhhc9 within the family. The compensate expression of Zdhhc14 may explain at least partially that inactivation of Zdhhc9 cannot completely inhibit the palmitoylation of Nras and block Nras leukemogenesis.

Example 8

Discussion

The present example further illustrates the demonstrations made by the preceding examples.

It has been previously shown that palmitoylation is essential for NRAS leukemogenesis, suggesting that targeting RAS palmitoylation may be an effective therapy at least for NRAS-related cancers.[9] Although KRAS4B is the major KRAS splice variant and does not undergo palmitoylation, it has been shown that KRAS4A, which relies on palmitoylation for its high-affinity plasma membrane binding, plays an essential role in the development of carcinogen induced lung cancer in mice and that oncogenic KRAS4A is widely expressed in human cancers.[30,31] The present invention demonstrates, among other things, that palmitoylacyltransferase Zdhhc9 functions as a RAS PAT in hematopoietic cells in vivo, though it is not the only one RAS PAT. Though no drastic effect on normal hematopoiesis and the overall survival of mice, Zdhhc9 inactivation prolongs the survival of mice with T-ALL and MPN induced by oncogenic Nras expressed from the endogenous locus. The findings suggest that ZDHHC9 may serve as a safe and effective target for developing therapies against RAS-driven cancers.

Human ZDHHC9 is highly expressed in brain,[18] and mutations in ZDHHC9 have been found in patients with X-linked mental retardation.[19] However, the Zdhhc9 knock-out mice grow normally as the wild-type ones and have no apparent abnormalities. It is possible that subtle neural disorders were not detected without special assays. Alternatively, it could be due to a difference between species. Detailed analysis of the effect of Zdhhc9 inactivation in neural development and physiology is warranted.

Zdhhc9 deficiency does not lead to drastic abnormalities in murine hematopoiesis, though it markedly represses Nras palmitoylation and disrupts NRAS localization on the plasma membrane in BM cells. A possible explanation is the functional redundancy of RAS family members. It is well documented that depletion of KRAS4A, HRAS and/or NRAS does not result in abnormal embryonic development in mice,[32-34] while only KRAS4B, mainly expressed isoform of KRAS, is indispensable in embryogenesis.[34,35] Therefore, nonpalmitoylated KRAS4B alone could functionally maintain normal hematopoiesis, even though all other RAS isoforms are inhibited by reducing palmitoylation. As such the side effects of the inhibitors targeting RAS PATs should be limited.

Interestingly, Zdhhc9 deficiency exhibits slight resistance to hematopoietic stress by 5-FU, suggesting that Zdhhc9 may play a role in stress response of hematopoietic cells. Since leukemia infiltration also exerts a stress on normal hematopoiesis,[36] targeting Zdhhc9 may both inhibit Nras transformation and protect normal hematopoiesis.

Zdhhc9 deficiency retards, but does not eliminate, the initiation of oncogenic Nras-induced leukemias, implicating that partial inhibition of NRAS palmitoylation is not sufficient for completely blocking NRAS leukemogenesis, as that of NRAS palmitoylation mutant. Due to the large gene family, co-expression of different Zdhhc genes in the same organ or tissue is common, which may lead to biological redundancy. Indeed, it is evident that ZDHHC family members have overlapping substrate specificities,[37] although many studied ZDHHC PAT family members exhibit a high degree of enzyme-substrate specificity.[18,3,39] It was shown that deletion of the Erf2 disrupted most but not all plasma membrane localization of Ras2 in yeast,[40,41] indicating that additional Ras-related PAT(s) exist. These findings, together with the observations shown herein that Zdhhc9 inactivation only partially inhibits Nras palmitoylation, indicate that there are more than one Ras PATs. Though inhibiting ZDHHC9 would have therapeutic benefits at least for NRAS-related cancers, identification of additional RAS PAT might help to develop stronger anti-cancer agents.

The effect of Zdhhc9 inactivation on Nras induced T-ALL appears to be stronger than that on Nras-induced CMML. Our data show that there are more expressions of Zdhhc9 subfamily genes in T lymphocytes. It is possible that T lymphocytes rely more on protein palmitoylation than that of myeloid cells, which may account, at least partially, the more severe phenotype of Zdhhc9 inactivation in Nras induced T-ALL compared to that of CMML.

TABLE 1

| Assays | Gene | NCBI RefSeq Accession No. | SEQ ID NO.: | Primer Name | Primer sequence (5'-3') | Product Length (bp) |
| --- | --- | --- | --- | --- | --- | --- |
| RT-qPCR For gene | Zdhhc1 | NM_175160 | 1 | F | ATGTGCGGGACAAGAGCTAC | 174 |
|  |  |  | 2 | R | GCCACTTGCAATGGTGATCG |  |

TABLE 1-continued

| Assays | Gene | NCBI RefSeq Accession No. | SEQ ID NO.: | Primer Name | Primer sequence (5'-3') | Product Length (bp) |
|---|---|---|---|---|---|---|
| Expression | Zdhhc2 | NM_178395 | 3 | F | TGTGCCTCATGGCTTATCATCT | 238 |
|  |  |  | 4 | R | TGGCATCTGTCACAATATCGGA |  |
|  | Zdhhc3 | NM_026917 | 5 | F | ATGCCACTAAAGAGTTCATCGAG | 128 |
|  |  |  | 6 | R | GCGAATGCACCGCTTACAA |  |
|  | Zdhhc4 | NM_028379 | 7 | F | GTGCCCACTTGCGATTTAAG | 213 |
|  |  |  | 8 | R | GTCACTAGGCGGAGCAGAAA |  |
|  | Zdhhc5 | NM_144887 | 9 | F | CCCAGGAATTTTTCCCCGAG | 113 |
|  |  |  | 10 | R | CACACCATTTCATTCGCACCT |  |
|  | Zdhhc6 | NM_001033573 | 11 | F | ACGTTCACACCATTGCAGAAA | 217 |
|  |  |  | 12 | R | CTTGACTGTGTTCCACCCAAA |  |
|  | Zdhhc7 | NM_133967 | 13 | F | TGCATCAAGCCGGAACGTGCC | 227 |
|  |  |  | 14 | R | GAGAAGTCGCTGCACTCTGTCCAC |  |
|  | Zdhhc8 | NM_172151 | 15 | F | TGGTTGGTTCCAGCACACTC | 138 |
|  |  |  | 16 | R | GGTCCATGAAGGTAGCCATACT |  |
|  | Zdhhc9 | NM_172465 | 17 | P1 | CCCATCTTGGACCAGGAACTG | 200 |
|  |  |  | 18 | P2 | GCGACACTCGAAGGCAAAGA |  |
|  | Zdhhc11 | NM_027704 | 19 | F | CGGTGATGGCACTGCTACTA | 184 |
|  |  |  | 20 | R | GGAAGGTCCCCCTTCTTCTG |  |
|  | Zdhhc12 | NM_001037762 | 21 | F | ACCCCGGCTATGTGACTACTC | 210 |
|  |  |  | 22 | R | TGCGTTCACCCACACAGTTC |  |
|  | Zdhhc13 | NM_028031 | 23 | F | ACTGGGCTGCCATTAACAACA | 129 |
|  |  |  | 24 | R | GCAAATGCCCTTGTCGGATG |  |
|  | Zdhhc14 | NM_146073 | 25 | F | ATCATTGGCCTTTCAGGTTTCC | 65 |
|  |  |  | 26 | R | ATGTCTTCGTTTGTGGTCTGG |  |
|  | Zdhhc15 | NM_175358 | 27 | F | GTGGAGTCGGAAACGTAGCA | 160 |
|  |  |  | 28 | R | GTGCAATGGAACACCCGAAC |  |
|  | Zdhhc16 | NM_023740 | 29 | F | TGGGCCTAATCTGGCTGA | 62 |
|  |  |  | 30 | R | GTATTTGCTGCGCTCATCCT |  |
|  | Zdhhc17 | NM_172554 | 31 | F | CGTCAAGGCGACACAATATGG | 70 |
|  |  |  | 32 | R | CCGTACATCGTAACCCGCTTC |  |
|  | Zdhhc18 | NM_001017968 | 33 | F | CTCAGGGTTCCACACGTACC | 198 |
|  |  |  | 34 | R | TCAGACTGCACGAATCCTCG |  |
|  | Zdhhc19 | NM_199309 | 35 | F | CGGGCTTTTTGATTCCGCTC | 159 |
|  |  |  | 36 | R | GTGGTGCAAACATTGCCAGA |  |
|  | Zdhhc20 | NM_029492 | 37 | F | GGAAAGACCGTTGTTTACCTTGT | 148 |
|  |  |  | 38 | R | ACTCCTTCTCATAACGCTCCTT |  |
|  | Zdhhc21 | NM_026647 | 39 | F | TGGTATTGAAGGGAGGCCCAT | 180 |
|  |  |  | 40 | R | CCCATTCTGCAGTCCTGTACC |  |
|  | Zdhhc22 | NM_001080943 | 41 | F | CTGCCCACTTCAATCAGCCA | 183 |
|  |  |  | 42 | R | TCTTACAGCCATCCCCTTTCG |  |
|  | Zdhhc23 | NM_001007460 | 43 | F | TGTTAGGGGTTCCTCCAGGG | 176 |
|  |  |  | 44 | R | TTGATICTCCGACGCAGCTA |  |
|  | Zdhhc24 | NM_027476.3 | 45 | F | AACTGGCGCTAGCTGCTTAT | 172 |
|  |  |  | 46 | R | GAGCAGTGACCACTACGAGG |  |
|  | Zdhhc25 | NM_027306 | 47 | F | TCCGGGACCTGCTTATACCA | 181 |
|  |  |  | 48 | R | TGGCAGTCGGTACAGTAGGA |  |
|  | Gapdh | NM_008084 | 49 | F | TGTGCAGTGCCAGCCTCGTC | 103 |
|  |  |  | 50 | R | GCCACTGCAAATGGCAGCCC |  |
| Genomic DNA PCR For Zdhhc9 KO mice | Zdhhc9-Exon2 | NC_000086.7 | 51 | P5 | GAAAGAAGGTGACACGGAAATG | P5 + P6 WT = 225 |
|  | Zdhhc9-Intron2 | NC_000086.7 | 52 | P6 | CAAATGCCCAGGAGGTACTGT |  |
| Genotyping | Zdhhc9-mutant | Selection Cassette LacZ/Neo | 53 | Neo | GCAGCGCATCGCCTTCTATC | Neo + P6 MUT = 203 |

REFERENCES

1. Plowman S J, Hancock J F. Ras signaling from plasma membrane and endomembrane microdomains. *Biochim Biophys Acta* 2005 Dec. 30; 1746(3): 274-283.
2. Pylayeva-Gupta Y, Grabocka E, Bar-Sagi D. RAS oncogenes: weaving a tumorigenic web. *Nature reviews Cancer* 2011 Nov. 1; 11(11): 761-774.
3. Stephen A G, Esposito D, Bagni R K, Mccormick F. Dragging Ras Back in the Ring. *Cancer Cell* 2014 Mar. 17; 25(3): 272-281.
4. Ward A F, Braun B S, Shannon K M. Targeting oncogenic Ras signaling in hematologic malignancies. *Blood* 2012 Aug. 16.
5. Zhang J, Ding L, Holmfeldt L, Wu G, Heatley S L, Payne-Turner D, et al. The genetic basis of early T-cell precursor acute lymphoblastic leukaemia. *Nature* 2012 Jan. 12; 481(7380): 157-163.
6. Hancock J F, Magee A I, Childs J E, Marshall C J. All ras proteins are polyisoprenylated but only some are palmitoylated. *Cell* 1989 Jun. 30; 57(7): 1167-1177.
7. Ahearn I M, Tsai F D, Court H, Zhou M, Jennings B C, Ahmed M, et al. FKBP12 binds to acylated H-ras and promotes depalmitoylation. *Molecular cell* 2011 Jan. 21; 41(2): 173-185.
8. Ahearn I M, Haigis K, Bar-Sagi D, Philips M R. Regulating the regulator: post-translational modification of RAS. *Nature reviews Molecular cell biology* 2011 Jan. 1; 13(1): 39-51.

9. Cuiffo B, Ren R. Palmitoylation of oncogenic NRAS is essential for leukemogenesis. *Blood* 2010 Apr. 29; 115(17): 3598-3605.
10. Harousseau J L. Farnesyltransferase inihibitors in hematologic malignancies. *Blood Rev* 2007 July; 21(4): 173-182.
11. James G L, Goldstein J L, Brown M S. Polylysine and CVIM sequences of K-RasB dictate specificity of prenylation and confer resistance to benzodiazepine peptidomimetic in vitro. *J Biol Chem* 1995 Mar. 17; 270(11): 6221-6226.
12. Nadolski M J, Linder M E. Protein lipidation. *Febs J* 2007 October; 274(20): 5202-5210.
13. Greaves J, Chamberlain L H. DHHC palmitoyl transferases: substrate interactions and (patho)physiology. *Trends in biochemical sciences* 2011 May; 36(5): 245-253.
14. Lakkaraju A K, Abrami L, Lemmin T, Blaskovic S, Kunz B, Kihara A, et al. Palmitoylated calnexin is a key component of the ribosome-translocon complex. *EMBO J* 2012 Apr. 4; 31(7): 1823-1835.
15. Bartels D J, Mitchell D A, Dong X, Deschenes R J. Erf2, a novel gene product that affects the localization and palmitoylation of Ras2 in Saccharomyces cerevisiae. *Mol Cell Biol* 1999 October; 19(10): 6775-6787.
16. Young E, Zheng Z Y, Wilkins A D, Jeong H T, Li M, Lichtarge O, et al. Regulation of Ras localization and cell transformation by evolutionarily conserved palmitoyltransferases. *Mol Cell Biol* 2014 February; 34(3): 374-385.
17. Tsutsumi R, Fukata Y, Fukata M. Discovery of protein-palmitoylating enzymes. Pflugers *Arch* 2008 September; 456(6): 1199-1206.
18. Swarthout J T, Lobo S, Farh L, Croke M R, Greentree W K, Deschenes R J, et al. DHHC9 and GCP16 constitute a human protein fatty acyltransferase with specificity for H- and N-Ras. *The Journal of biological chemistry* 2005 Sep. 2; 280(35): 31141-31148.
19. Raymond F L, Tarpey P S, Edkins S, Tofts C, O'Meara S, Teague J, et al. Mutations in ZDHHC9, which encodes a palmitoyltransferase of NRAS and HRAS, cause X-linked mental retardation associated with a Marfanoid habitus. *American journal of human genetics* 2007 May 1; 80(5): 982-987.
20. Mansilla F, Birkenkamp-Demtroder K, Kruhoffer M, Sorensen F B, Andersen C L, Laiho P, et al. Differential expression of DHHC9 in microsatellite stable and instable human colorectal cancer subgroups. *Br J Cancer* 2007 Jun. 18; 96(12): 1896-1903.
21. Haigis K M, Kendall K R, Wang Y, Cheung A, Haigis M C, Glickman J N, et al. Differential effects of oncogenic K-Ras and N-Ras on proliferation, differentiation and tumor progression in the colon. *Nature Genetics* 2008 May 1; 40(5): 600-608.
22. Wang J, Liu Y, Li Z, Du J, Ryu M J, Taylor P R, et al. Endogenous oncogenic Nras mutation promotes aberrant GM-CSF signaling in granulocytic/monocytic precursors in a murine model of chronic myelomonocytic leukemia. *Blood* 2010 Dec. 23; 116(26): 5991-6002.
23. Wang J, Liu Y, Li Z, Wang Z, Tan L X, Ryu M-J, et al. Endogenous oncogenic Nras mutation initiates hematopoietic malignancies in a dose- and cell type-dependent manner. *Blood* 2011 Jul. 14; 118(2): 368-379.
24. Wan J, Roth A F, Bailey A O, Davis N G. Palmitoylated proteins: purification and identification. *Nature protocols* 2007 Jan. 1; 2(7): 1573-1584.
25. Gross A W, Zhang X, Ren R. Bcr-Abl with an SH3 deletion retains the ability To induce a myeloproliferative disease in mice, yet c-Abl activated by an SH3 deletion induces only lymphoid malignancy. *Molecular and cellular biology* 1999 Oct. 1; 19(10): 6918-6928.
26. Flex E, Petrangeli V, Stella L, Chiaretti S, Hornakova T, Knoops L, et al. Somatically acquired JAK1 mutations in adult acute lymphoblastic leukemia. *J Exp Med* 2008 Apr. 14; 205(4): 751-758.
27. Loh M L. Recent advances in the pathogenesis and treatment of juvenile myelomonocytic leukaemia. *Br J Haematol* 2011 March; 152(6): 677-687.
28. Ricci C, Fermo E, Corti S, Molteni M, Faricciotti A, Cortelezzi A, et al. RAS mutations contribute to evolution of chronic myelomonocytic leukemia to the proliferative variant. *Clin Cancer Res* 2010 Apr. 15; 16(8): 2246-2256.
29. Tyner J W, Erickson H, Deininger M W, Willis S G, Eide C A, Levine RL, et al. High-throughput sequencing screen reveals novel, transforming RAS mutations in myeloid leukemia patients. *Blood* 2009 Feb. 19; 113(8): 1749-1755.
30. To M D, Wong C E, Karnezis A N, Del Rosario R, Di Lauro R, Balmain A. Kras regulatory elements and exon 4A determine mutation specificity in lung cancer. *Nature Genetics* 2008 Oct. 1; 40(10): 1240-1244.
31. Tsai F D, Lopes M S, Zhou M, Court H, Ponce O, Fiordalisi J J, et al. K-Ras4A splice variant is widely expressed in cancer and uses a hybrid membrane-targeting motif. *Proceedings of the National Academy of Sciences of the United States of America* 2015 Jan. 20; 112(3): 779-784.
32. Umanoff H, Edelmann W, Pellicer A, Kucherlapati R. The murine N-ras gene is not essential for growth and development. *Proceedings of the National Academy of Sciences of the United States of America* 1995 Feb. 28; 92(5): 1709-1713.
33. Ise K, Nakamura K, Nakao K, Shimizu S, Harada H, Ichise T, et al. Targeted deletion of the H-ras gene decreases tumor formation in mouse skin carcinogenesis. *Oncogene* 2000 Jun. 15; 19(26): 2951-2956.
34. Plowman S J, Williamson D J, O'Sullivan M J, Doig J, Ritchie A-M, Harrison D J, et al. While K-ras is essential for mouse development, expression of the K-ras 4A splice variant is dispensable. *Molecular and cellular biology* 2003 Dec. 1; 23(24): 9245-9250.
35. Koera K, Nakamura K, Nakao K, Miyoshi J, Toyoshima K, Hatta T, et al. K-ras is essential for the development of the mouse embryo. *Oncogene* 1997 Sep. 4; 15(10): 1151-1159.
36. Cheng H, Hao S, Liu Y, Pang Y, Ma S, Dong F, et al. Leukemic marrow infiltration reveals a novel role for Egr3 as a potent inhibitor of normal hematopoietic stem cell proliferation. *Blood* 2015 Jul. 17.
37. Hou H, John Peter A T, Meiringer C, Subramanian K, Ungermann C. Analysis of DHHC acyltransferases implies overlapping substrate specificity and a two-step reaction mechanism. *Traffic* 2009 August; 10(8): 1061-1073.
38. Fukata Y, Iwanaga T, Fukata M. Systematic screening for palmitoyl transferase activity of the DHHC protein family in mammalian cells. *Methods* 2006 October; 40(2): 177-182.
39. Iwanaga T, Tsutsumi R, Noritake J, Fukata Y, Fukata M. Dynamic protein palmitoylation in cellular signaling. *Frog Lipid Res* 2009 May-July; 48(3-4): 117-127.
40. Hou H, Subramanian K, LaGrassa T J, Markgraf D, Dietrich LE, Urban J, et al. The DHHC protein Pfa3

41. Zhao L, Lobo S, Dong X, Ault A D, Deschenes RJ. Erf4p and Erf2p form an endoplasmic reticulum-associated complex involved in the plasma membrane localization of yeast Ras proteins. *J Biol Chem* 2002 Dec. 20; 277(51): 49352-49359.

affects vacuole-associated palmitoylation of the fusion factor Vac8. *Proc Natl Acad Sci USA* 2005 Nov. 29; 102(48): 17366-17371.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A method of reducing incidence and severity of hematopoietic stress in a subject who is receiving or has received chemotherapy and is suffering from or susceptible to such hematopoietic stress, the method comprising:
   administering a ZDHHC9 siRNA to the subject
      wherein the chemotherapy comprises administration of a chemotherapeutic agent selected from the group comprising fluorouracil, vincristine, doxorubicin, cyclophosphamide, L-asparaginase, methotrexate, cytarabine, imatinib, dasatinib, azacitidine, 6-mercaptopurine, decitabine, idrarubicin, and fludarabine.

2. The method of claim 1, wherein the chemotherapy comprises or consists of administration of fluorouracil.

3. The method of claim 1, wherein the ZDHHC9 siRNA is administered prior to initiation of the chemotherapy.

4. The method of claim 1, wherein the ZDHHC9 siRNA is administered prior to development of the hematopoietic stress.

5. The method of claim 1, wherein the ZDHHC9 siRNA is administered substantially concurrently with one or more chemotherapy doses.

6. The method of claim 1, wherein the ZDHHC9 siRNA is administered after one or more chemotherapy doses.

7. The method of claim 1, wherein the ZDHHC9 siRNA is administered after development of the hematopoietic stress.

8. The method of claim 1, wherein the subject is suffering from a cancer associated with hyperactivation of a RAS family member.

9. The method of claim 1, wherein the subject is suffering from a cancer determined to express a palmitoylate.

* * * * *